US005670151A

United States Patent [19]
Larrick et al.

[11] Patent Number: 5,670,151
[45] Date of Patent: Sep. 23, 1997

[54] METHOD FOR CONTROLLING HYPERPROLIFERATIVE DISEASES

[75] Inventors: James W. Larrick, Woodside; L. L. Houston, Oakland; Eric S. Groves, Lafayette, all of Calif.

[73] Assignee: Chiron Corporation, Emeryville, Calif.

[21] Appl. No.: 807,951

[22] Filed: Dec. 10, 1991

Related U.S. Application Data

[63] Continuation of Ser. No. 436,538, Nov. 14, 1989, abandoned, which is a continuation-in-part of Ser. No. 856,731, Apr. 28, 1986, abandoned.

[51] Int. Cl.$^6$ .................. A61K 39/395; A61K 39/40; A61K 39/42; A61K 39/44
[52] U.S. Cl. .................. 424/183.1; 424/143.1; 424/178.1; 530/388.22
[58] Field of Search .................. 424/143.1, 178.1, 424/183.1; 530/388.22

[56] References Cited

U.S. PATENT DOCUMENTS

| | | | |
|---|---|---|---|
| 4,434,156 | 2/1984 | Trowbridge | 424/143.1 |
| 4,830,962 | 5/1989 | Gelfand et al. | 435/69.6 |
| 4,894,443 | 1/1990 | Greenfield et al. | 530/388.22 |

OTHER PUBLICATIONS

Fulcher, S. et al. (II), "Use of Immunotoxin to Inhibit Proliferating Human Corneal Endothelium," *Invest. Ophthalmol. Visual. Sci.* 29(5): 755–759, May 1988.

Trowbridge, I.S. et al. "Anti–transferrin receptor monoclonal antibody and toxin—antibody conjugates affect growth of human tumor cells," *Nature* 294: 171–173, Nov. 12, 1981.

Ramakrishan, S., 1984, *Science*, 223:58–61.

Van Bockxmeer, F.M. et al., 1982, *J. Tissue Culture Methods*, 7:163–167.

Fastenberg, D.M, et al., 1982, *Am. J. Ophthalmol.*, 93: 565–572.

Fastenberg, D.M., et al., 1982, *Am. J. Ophthalmol.*, 93:559–564.

Fulcher, S., et al., (I), "Effect of an Immunotoxin Containing Ricin A Chain and Monoclonal Antibody Against the Transferrin Receptor on the Proliferation of Human Corneal Endothelium", Annual Spring Meeting of the Association for Research in Vision and Ophthamology Incorporated, Sarasota, Fla, USA, Apr. 28–May 2, 1986, *Invest Ophthalmology Visual Science,*27 (3 Suppl.):69, 1986.

*Primary Examiner*—Toni R. Scheiner
*Assistant Examiner*—Sheela J. Huff
*Attorney, Agent, or Firm*—Thomas P. McCracken; Grant D. Green; Robert P. Blackburn

[57] ABSTRACT

A method for controlling the overgrowth of hyperproliferating cells in the presence of non-proliferating cells by exposing the hyperproliferating cells to a toxin conjugate that has a binding region that binds to an internalizable element of the hyperproliferating cell and a toxic moiety bound thereto is provided. The toxin conjugate may be a monoclonal antibody to transferrin receptor. Such toxin conjugates will have use in controlling hyperproliferative diseases of the integument and the eye.

10 Claims, 13 Drawing Sheets

FORM FOR GRADING RETINAL DAMAGE IN RABBIT PVR MODEL

Week After Injection: 1, 2, 3, 4, 5, 6, 7, 8, 9, 10, 11, 12

ANIMAL MODEL FOR PRERETINAL MEMBRANES    BLOOD:  tr  mod  heavy

1. ____+ Single Stalk Extending up from the Injection Site. Any growth from stalk into the vitreous or to the ray, nerve, or retinal surface is 2+. If height is not 4 to 5 disc diameters and circumferences is not 0.5 disc diameters, it should be graded at less the 1+. 1.9+ extends to midvitreous. 1+ to 1.9+ extend between 4 dd and midvitreous.

2. ____+ Multiply Stalks or a Single Stalk Extending to Another Structure. Visable traction sufficient to cause detachment of the ray or retina are graded 3+ or 4+.

3. ____+ Traction Sufficient to Cause Detachment of the Ray. Any traction causing a retinal detachment is graded as 4+. If both sides of the ray are detached it must be graded 3.7 to 3.9+.

4. ____+ Traction Detachment of a Least a Small Area of the Retina.

VITREOUS GRADE                                        (check one)

____ 0.0 + clear;                           ____ 1.0 + mild hazy;

____ 2.0+ very hazy but all structures are visable;

____ 3.0+ not all structures are visable;

____ 4.0+ no visable structures.

____ Vg = Growth in vitreous away from the puncture site.

____ P = Plaquoid growth on the retina.

____ Small spot dd or less

____ Moderate                              ____ Extensive

FIG. 13

RABBIT MODEL OF PVR GROWTH FORM

0 PLUS = No growth. Amount of growth less than 1 plus are graded 0.1 to 0.9

0.1 —— 0.2 —— 0.3 —— 0.4 —— 0.5 —— 0.6 —— 0.7 —— 0.8 —— 0.9 ——

* 1 plus = Intravitreal membranes extending at least 5 disc diameters into the vitreous from the injection site or a localized area of proliferation of membranes 5 disc diameters or more.

0.1 —— 0.2 —— 0.3 —— 0.4 —— 0.5 —— 0.6 —— 0.7 —— 0.8 —— 0.9 ——

* 2 plus = Intravitreal membranes extending to the retina, optic nerve, or medullary ray from the vitreous or retinal surface 0.1 —— 0.2 —— 0.3 —— 0.4 —— 0.5 —— 0.6 —— 0.7 —— 0.8 —— 0.9 ——

* 3 plus = Detachment of the medullary ray (Must be 3.6 or more if both medullary rays are detached)

0.1 —— 0.2 —— 0.3 —— 0.4 —— 0.5 —— 0.6 —— 0.7 —— 0.8 —— 0.9 ——

* 4 plus = Detachment of the retina 0.1 —— 0.2 —— 0.3 —— 0.4 —— 0.5 —— 0.6 —— 0.7 —— 0.8 —— 0.9 ——

FIG. 14

METHOD FOR CONTROLLING HYPERPROLIFERATIVE DISEASES

This application is a continuation of application Ser. No. 07/436,538, filed Nov. 14, 1989 now abandoned, which is a continuation-in-part of U.S. patent application Ser. No. 06/856,731, filed Apr. 28, 1986, with the Patent and Trademark Office now abandoned.

FIELD OF THE INVENTION

The disclosed invention relates to methods of reducing hyperproliferating cells and to the treatment of hyperproliferative diseases of the integument, eye and other body parts.

BACKGROUND OF THE INVENTION

Hyperproliferation of cells in an organism may lead to a variety of diseases in patients. The particular disease symptoms will vary depending on the cell type of the hyperproliferative cell and the tissue where the cell is located. These states may range from cancerous malignancies when the cell is a cancer cell to scarring when the cell type is a normal endothelial fibroblast or a skin disease when the hyperproliferating cell is an epithelial or dermal cell forming a part of the organism's integument or skin.

Hyperproliferation of cells in various tissues of the eye can lead to impaired vision. As a result of injuries to the eye, for example due to penetration, various cells of the eye proliferate during the healing process. When such proliferating cells of the eye hyperproliferate, the cells frequently overgrow the healing regions resulting in impaired vision, and in extreme cases, blindness.

Abnormal cellular proliferative disease of the eye are typified by down growth of the epithelium into the anterior chamber of the eye and a condition termed vitreoretinopathy. In the first of these conditions, epithelial down growth, the anterior chamber of the eye is primarily affected. Epithelial cells, typically derived from the corneal or conjunctival cells of the eye, grow into the anterior chamber of the eye, resulting in a number of conditions including a reactive inflation of the uvea, which is the colored vascular layer of the eye including the iris, ciliary body and choroid. Another condition, peripheral anterior synechia, is characterized by adhesion of the base of the iris to the cornea. This condition frequently causes a partial closing of the angle of the anterior chamber of the eye resulting in glaucoma. In some instances, epithelial down growth results in the formation of a complete cell layer in the anterior chamber. In extreme cases, the eye may atrophy and shrink. In all of these conditions caused by inappropriate hyperproliferation of normal, as opposed to malignant, epithelial cells of the eye, blindness may result.

The second form of hyperproliferative disease of the eye, proliferative vitreoretinopathy (PVR), is a frequent complication of traumatic injury to the eye, traumatic or spontaneous retinal detachment, and surgery to correct detachment of the retina. In this disorder, migrating retinal pigment epithelial (RPE) cells and glial cells from the retina become established at the junction of the retina and the vitreous chamber, a portion of the posterior chamber of the eye. RPE cells formed part of the blood retinal barrier. They lie between the Brach's membrane and the choroid, and the outer segments of the photoreceptors cells. Under normal circumstances, these cells do not proliferate in vivo. However, they hyperproliferate under various pathological conditions that include PVR. In PVR, the RPE of Several different lineages undergo a process of differentiation, often breaking free from the underlying tissues and growing and dividing in the vitreous humor.

Further, as a result of proliferation of these cells, a secondary membrane may form. These membranes lead to changes in the retinal cells, impairment of visual acuity, retinal perforation, retinal detachment and blindness. This condition is the primary cause of failure of retinal reattachment surgery and at present the condition cannot be successfully treated in the vast majority of cases. Chemotherapy or surgery, including laser treatments, are the usual treatment for PVR but surgical removal of differentiated tissue often fails to stop further aberrant cellular proliferation while chemotherapy using, for example, 5-flurouracil is nonspecific and damages normal cells.

Another form of proliferative disorder of the eye is diabetes associated proliferative retinopathy. This disorder is a complication of diabetes and is seen most frequently in insulin-dependent diabetics. The disorder is characterized by a proliferation of weakened abnormal blood vessels that grow on the surface of the retina and into the vitreous chamber of the eye. Hemorrhages into the vitreous chamber are associated with these blood vessels and retinal detachment may also occur.

The formation of pterygium is another form of proliferative disorder of the eye that is caused by hyperproliferation of cells. Pterygium forms an abnormal structure on the surface of the globe of the eye. The pterygium extends from the conjunctiva to the cornea and is usually a triangular shaped piece of tissue. It grows over and destroys the corneal surface. When the pterygium reaches the central 3 mm of the cornea, the visual axis is threatened, resulting in vision problems or blindness. This condition is traditionally corrected by surgery. However, the main drawback of surgery is the regrowth of the pterygium and the need for repeated surgery. The regrowth occurs at a variable rate, but about 10% of the surgeries will fail because of immediate regrowth of the pterygium. Currently, there is no effective treatment to prevent regrowth. The present treatments include irradiation done at the time of surgery or treatment with 5-fluorouracil (5-Fu), mitomycin c, or thiotepa (an alkylating reagent), which are severely toxic chemicals.

Proliferative eye disorders are also a complication in a significant number of cataract or lens extraction surgeries. For example, in glaucoma treatment, a drainage passage in the eye is surgically created to drain excess fluid from the eye. The passage must remain open to reduce the pressure within the eye. Currently, 5-FU is used to prevent closure of the drainage passage from the anterior chamber into the subconjunctival space. However, 5-FU is not effective for very long. Proliferating cells also result in scarring, for example, in the case of cicatricial penthagoid.

Many types of proliferating cells are known to have increased activity of transferrin receptors. Transferrin receptors are sites protein expressed on cell surface on the cell to which an iron-carrying protein called transferrin bind. Growing proliferating cells generally have an increased requirement for iron. This requirement is met by increasing the transport of iron via the transferrin-transferrin receptor complex. The transferrin receptor with bound transferrin is internalized by the cell and transferrin is eventually released from the internalized transferrin receptor at the endosomal level under acidic environment. Transferrin receptors are recycled appearing at the cell surface where transferrin is once again bound and eventually internalized and released. To meet the increased requirements of cell growth, transferrin receptor activity of the growing cell increases. It has been suggested that the increased transferrin receptor activity may be due either to a faster turnover of the transferrin receptor as it cycles between external binding and internal release of transferrin or an increase in the number of transferrin receptors carried by the growing cell or both.

The differences in the level of activity of transferrin receptor in growing cells is also reflected in the process of cell differentiation. Cell differentiation is the process by which cells mature and usually entails a series of cell divisions and cell proliferation in the course of the maturation process. Cells in their mature form are frequently non-proliferating and as a result, do not have increased transferrin receptor activity. Cells that have not completed differentiation from a progenitor cell type into a mature form, continue to proliferate and frequently have increased transferrin receptor activity. For example, red blood cells and leukocytes found in the circulating blood arise from progenitor stem cells in the bone marrow. Stem cells in the bone marrow are undifferentiated and frequently divide actively, whereas red blood cells and leukocytes are normally non-proliferating as mature cells in the blood stream, and do not have high transferrin receptor activity. One of the characteristics of dividing cancer tumor cells is an apparent loss of terminal differentiation and the comparatively rapidly dividing proliferating cancer cells frequently have high levels of transferrin receptor activity.

Monoclonal antibodies to transferrin receptor are known and are able to bind to transferrin receptor. A murine monoclonal antibody to transferrin receptor that blocks the binding of transferrin to the receptor in CCRF-CEFM cells has been disclosed in U.S. Pat. No. 4,434,156. A number of uses of this transferrin blocking anti-transferrin receptor monoclonal antibody are suggested, including its use as a diagnostic material to indicate the presence of tumor cells. The complement mediated destruction of tumor cells by the anti-transferrin receptor monoclonal antibody is suggested as a therapy for killing tumor cells. The use of such antibodies carrying toxins such as ricin is also suggested as a method to destroy tumor cells. It is also suggested that the use of the anti-transferrin receptor monoclonal antibody is effective in interfering with growth of known tumor cells by starving such tumor cells of iron, or arresting their growth in a manner making the cells sensitive to chemotherapy. The disclosure of U.S. Pat. No. 4,434,156 does not, however, address the use of toxic conjugates of antibodies to the translenin receptor as a therapeutic to treat proliferating non-tumorous cells.

As has been alluded to above, a number of hyperproliferative disorders of non-malignant cells are known. These hyperproliferating cells grow in the presence of surrounding normal non-proliferating tissues, the function of which may be severely disrupted by the hyperproliferating tissue. It would be desirable to be able to control the growth of the hyperproliferating tissue without detrimentally affecting the surrounding non-proliferating tissue, and thus prevent or reduce the disruption of normal function.

Injuries to the eye often result in proliferation of cells or overgrowth that disrupts normal tissue relationships and may result in blindness. It is possible to use regional treatment of proliferative eye disorders to prevent overgrowth that results from injury, retinal detachment, or other disease. Because confluent cells are more resistant than rapidly proliferating cells, most of the cells in the eye will not be affected by the immunotoxin. Only the rapidly proliferating cells that are the eventual cause of blindness will be affected. Because only small concentrations and very small absolute mounts of the immunotoxin are used, the danger of toxic effects to the patient will be very small. The relatively rapid rate of replacement of the material in the anterior and vitreous chambers of the eye serves to reduce the concentrations of the immunotoxin after application. This also provides a safety factor by clearing the immunotoxin after a sufficient time has elapsed for the molecule to diffuse and bind to target cells. Immunotoxins are known to require only a short time to bind to target cells, and then excess immunotoxin can be removed without impairing the efficiency of the eventual killing of the cell.

It has been found that by exposing hyperproliferating cells to a toxin conjugate that specifically binds to an internalizable reduce the viability of the element of the proliferating cells. It has been further discovered that some cells when present in a non-proliferating state, are essentially unaffected when exposed to a like toxin conjugate at a like concentration.

BRIEF DESCRIPTION OF THE INVENTION

The disclosed invention is a method for killing hyperproliferating cells by exposing such cells to a concentration of a toxin conjugate sufficient to kill such cells wherein the toxin conjugate comprises a toxic moiety and a binding region that binds to the proliferating cell and is internalized.

In one embodiment, the invention is for a method of controlling non-cancerous hyperproliferative cells by exposing such non-cancerous hyperproliferative cells to a concentration of a toxin conjugate sufficient to kill the hyperproliferative cells when the toxin conjugate comprises a toxic moiety and a binding region that binds to an internalizable element of the normal hyperproliferating cell.

In a further embodiment of the invention, the hyperproliferating cell is a human cell of epithelial or endothelial origin and the toxin conjugate comprises an antibody that binds to the transferrin receptor of the hyperproliferative cell.

In another embodiment of the invention, the hyperproliferating cell is ocular epithelial or endothelial origin.

In another aspect, the invention comprises a toxic conjugate comprising a toxin portion and binding portion capable of binding to an internalizable element of the cell in a pharmaceutically acceptable carrier suitable for parenteral topical use.

The invention described herein draws on previous work, including scientific papers, patents, and pending patent applications. All of these publications and applications as cited previously and below are hereby incorporated by reference in their entireties.

BRIEF DESCRIPTION OF THE DRAWINGS

The invention will be better understood in connection with the following figures.

FIG. 13 presents the criteria for grading retinal damage in rabbit PVR model.

FIG. 14 presents the form for evaluating growth of PVR in rabbit model.

DETAILED DESCRIPTION OF THE INVENTION

Figure 1:
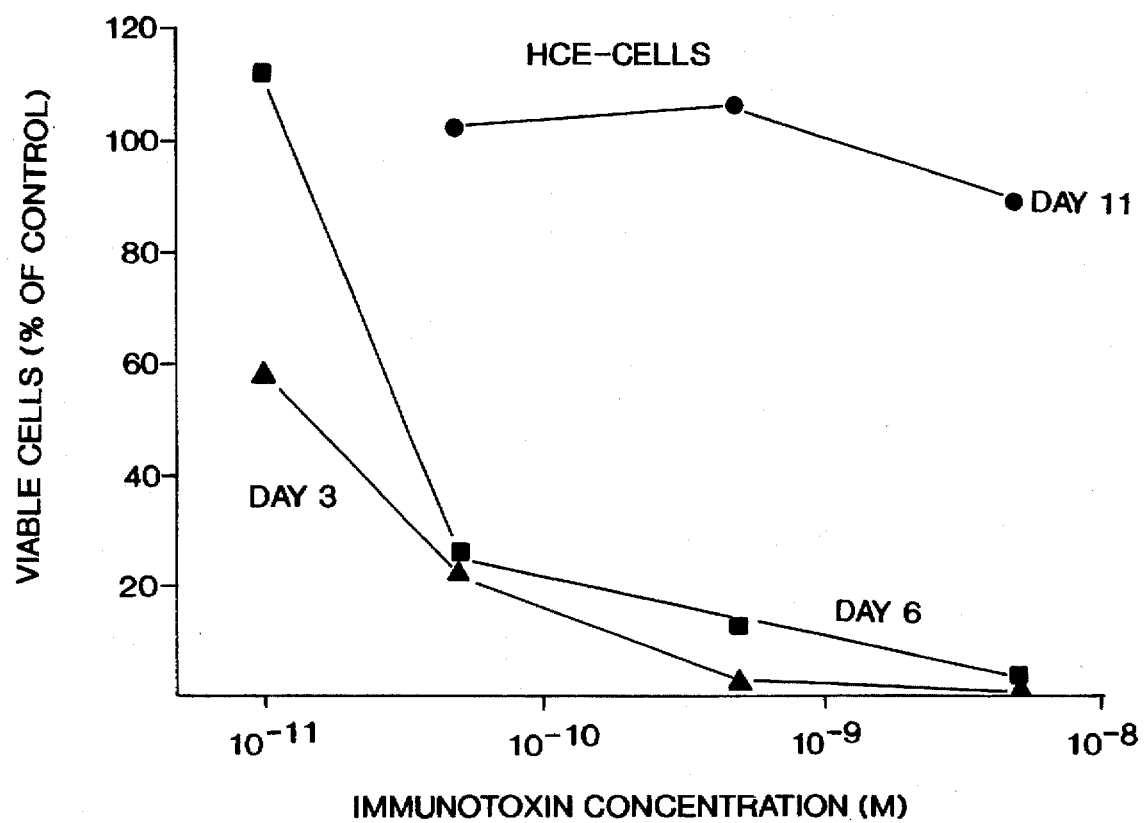
FIG. 1 is a survival curve of corneal epithelial cells treated once for 7 days with a toxic conjugate of an anti-transferrin monoclonal antibody linked to recombinant ricin A chain after 3, 6, or 11 days of growth.
Figure 2A:
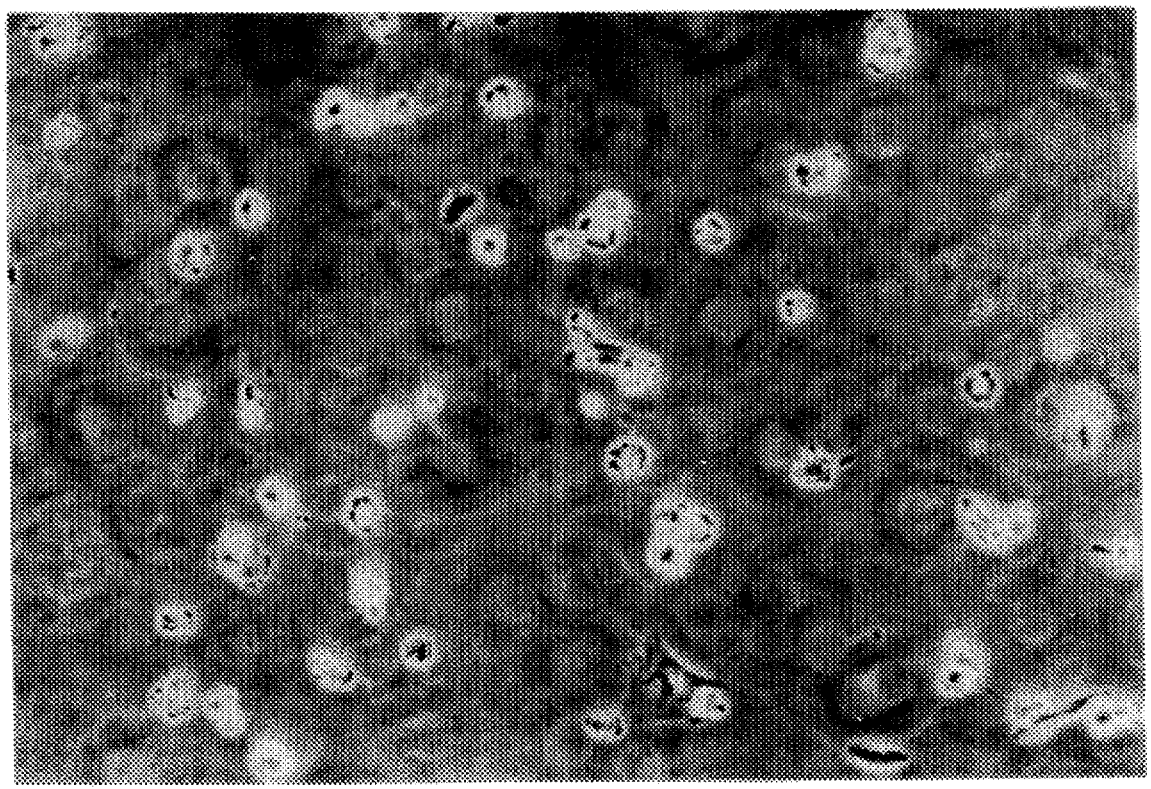
FIG. 2A is a photomicrograph of a culture of human corneal endothelial cells grown for 6 days and then cultured for 7 days in the presence of 5×10–9M (0.9 μg/ml) of anti-transferrin monoclonal antibody linked to recombinant ricin toxin A chain.
Figure 2B:
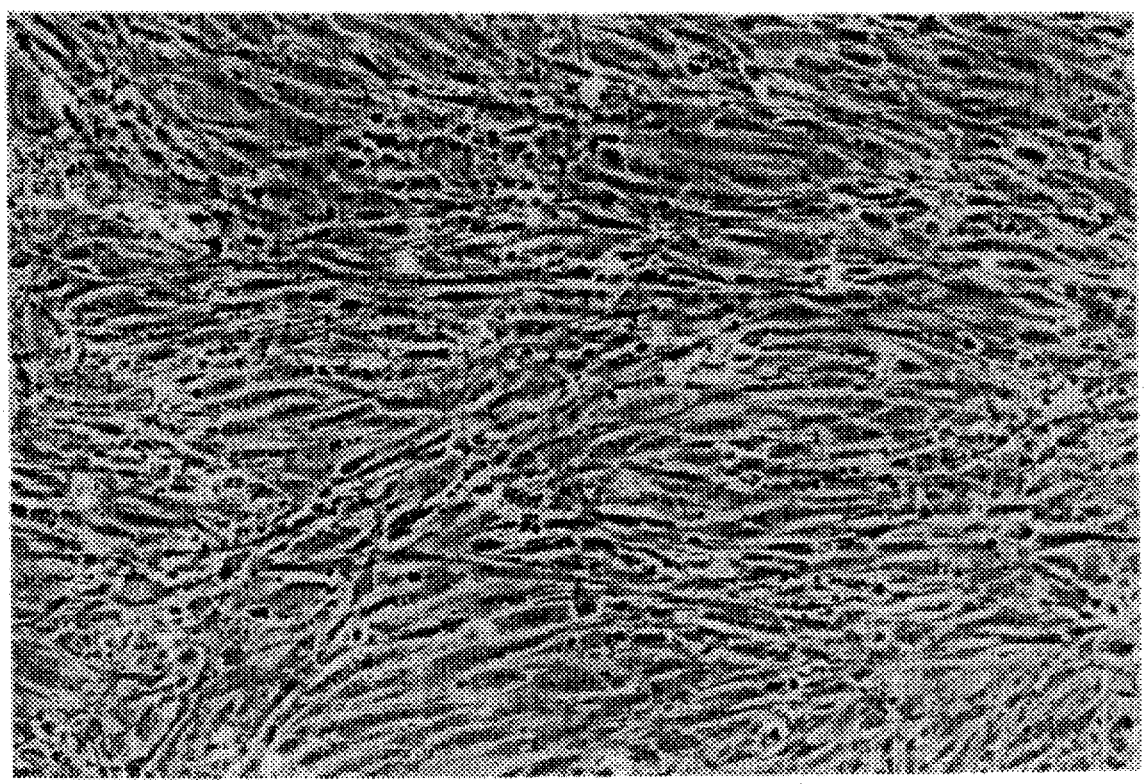
FIG. 2B is a photomicrograph of a culture of human corneal endothelial cells grown for 11 days and then treated for 7 days with 5×10–9M (0.9 μg/ml of anti-transferrin monoclonal antibody linked to recombinant ricin Toxin A chain).
Figure 2C:
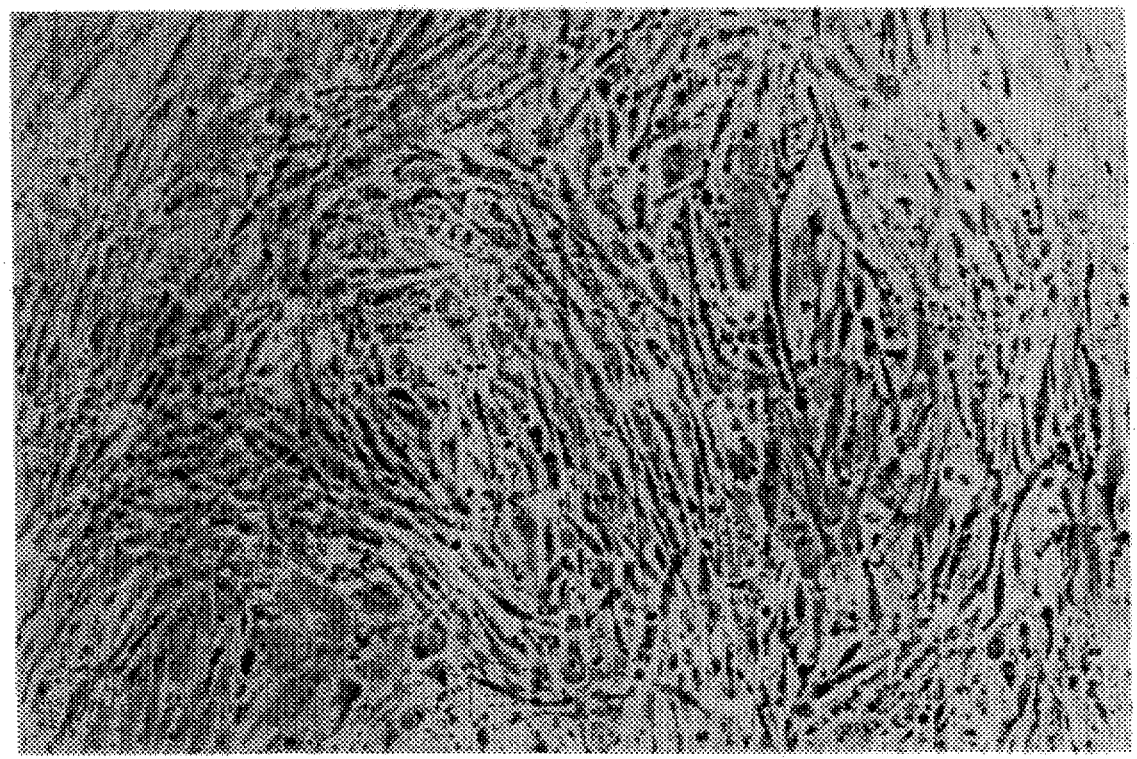
FIG. 2C is a photomicrograph of an untreated 11 day culture as a control.

The present invention is generally applicable to non-malignant hyperproliferative diseases. The present invention applies generally to any situation in which proliferating cells create pathological or undesirable conditions. Such diseases may affect the integument and are typified by hyperproliferative disease of the skin, such as psoriasis, keloid scarring, and various keratoses. In addition, benign papillomas occurring in various hollow organs of the body are intended to be within the scope of the invention. Furthermore, hyperproliferative diseases of the eye including epithelial down growth; vitreoretinopathy; diabetic retropathy; complications of eye surgeries, for example, in cataract, glaucoma, or lens extraction surgeries, as in the case of glaucoma surgery in which the cells regrow and block the drainage passage which has been surgically created to drain excess fluid from the eye; scarring, for example, in cicatricial penthagoid; and pterygium are also considered within the scope of the invention.

The toxin conjugate according to the method of the invention comprises a toxic moiety and a binding region, which binds to an internalizable element of the proliferating cell or which is itself internalizable. The internalizable element of the cell will generally be located at the cell surface during some portion of the cell growth cycle. The internalizable element may be a specific receptor that is active at elevated levels during cell growth. Such receptors include transferrin receptor or the receptor for epidermal growth factor.

The part of the receptor that is bound by the binding region may vary. The part of the receptor that is bound by the binding region may be an antigenic region of the receptor that is recognized by a specific antibody, preferably a monoclonal antibody. The part of the receptor bound may alternatively be the region of the receptor that actively binds to the material normally bound by the receptor or may be an antigen in that region.

The binding portion of the conjugate will specifically bind to the internalizable element. Such binding portions may be an antibody or the antigen binding portion thereof which binds to an antigen that is part of the internalizable element. If the internalizable element is a receptor, the binding portion may be an antibody or antigen binding portion thereof that binds to an antigen which is part of the receptor. Such antigens may be located in an area of the receptor such that when the binding portion of the toxic conjugate is bound to the receptor, it does not prevent or significantly reduce the binding of the material for which the receptor is specific. In the case of the transferrin receptor, it is preferred that the binding portion is an antibody, preferably a monoclonal antibody, that binds to an antigen of the transferrin receptor in such a manner that binding of transferrin to the receptor occurs. Less preferred are antibodies or antigen binding portions thereof that bind to antigens to the transferrin receptor that prevent or measurably inhibit the binding of transferrin receptor to the monoclonal antibody.

As used herein, "antibody" is intended to mean a polyclonal or monoclonal antibody.

As used herein, "antibody" is intended to mean a polyclonal or monoclonal antibody.

As used herein, the term "monoclonal antibody" means an antibody composition having a homogeneous antibody population. It is not intended to be limited as regards the source of the antibody or the manner in which it is made.

As used herein the term "antigen binding portion of an antibody" means the portion of the antibody that binds an antigen to which the antibody is specific. In general, such antigen binding portions of the antibody encompass the Fab, Fab' and F(ab')$_2$ regions or fragments of the immunoglobin molecule. Fab, Fab' and F(ab')$_2$ regions of an immunoglobin may be generated by enzymatic digestion of the antibodies using techniques well known to those skilled in the art. Fab fragments may be generated by digesting the antibody with papain and contacting the digest with a reducing agent to reductively cleave disulfide bonds. Fab' fragments may be obtained by digesting the antibody with pepsin and reductive cleavage of the fragment so produced with a reducing agent. In the absence of reductive cleavage, enzymatic digestion of the antibody with pepsin produces F(ab')$_2$ fragments.

Antibodies to the internalizable element of the proliferating cell are the preferred binding component according to the invention. In addition, the binding portion of the conjugate may be a material, other than an antibody to an antigen on the internalizable element, that ordinarily binds to the internalizable element and is itself ordinarily internalized. Thus, transferrin itself may be used as the binding portion of the conjugate. Epidermal growth factor could also be used in an analogous manner. The internalizable element of the hyperproliferating cell will usually be found at the surface of the cell during a portion of the cell growth cycle and is internalized into the cell daring another portion of the cell growth cycle. Internalization of the element may take place either periodically or in response to a stimulus such as the binding to the receptor of a material for which it is specific.

The toxin conjugate according to methods of the invention are conjugates of the binding portion and a cytotoxic moiety. The cytotoxic moiety of the toxin conjugate may be a cytotoxic drug or an enzymatically active toxin of bacterial, fungal or plant origin, or an enzymatically active polypeptide chain or fragment ("A chain") of such a toxin. Enzymatically active toxins and fragments thereof are preferred and are exemplified by diphtheria toxin A fragment, and especially non-binding active fragments of diphtheria toxin, exotoxin A (from *Pseudomonas aeruginosa*), ricin A chain, abrin A chain, modecein A chain, alpha-sarcin, certain *Aleurites fordii* proteins, certain Dianthin proteins, *Phytolacca americana* proteins (PAP, PAPII and PAP-S), *Momordica charantia* inhibitor, curcin, crotin, *Saponaria officinalis* inhibitor, gelonin, mitogellin, restrictocin, phenomycin, and neomycin. Ricin A chain, *Pseudomonas aeruginosa* exotoxin A and PAP are preferred.

Conjugates of the binding portion, particularly when it is an antibody and such cytotoxic moieties may be made using a variety of bi-functional protein coupling agents. Examples of such reagents are N-succinimidyl-3-(2-pyridyldithio) propionate (SPDP), iminothiolane (IT), bi-functional derivatives of imidoesters such as dimethyl adipimidate. HCl, active esters such as disuccinimidyl suberate, aldehydes such as glutaraldehyde, bis-azido compounds such as bis(p-diazoniumbenzoyl)-ethylenediamine, diisocyanates such as tolylene 2,6-diisocyante, and bis-active fluorine compounds such as 1,5-fluoro-2,4-dinitrobenzene.

The enzymatically active polypeptide of the toxin conjugate according to the invention may be recombinantly produced. The plasmid, designated pRA123, encoding the entire sequence for ricin A has been deposited with the American Type Culture Collection (ATCC), 12301 Parklawn Drive, Rockville, Md. 20852, U.S.A., under the Budapest Treaty on the International Recognition of the Deposit of Microorganisms for the Purposes of Patent Procedure and Regulations Thereunder (Budapest Treaty) and are thus made, maintained and made available according to the Budapest Treaty. The plasmid was deposited at the ATCC on Aug. 14, 1984, with the Accession No. 39799, plasmid pRA123 contains the entire sequence for ricin A, as confirmed by sequencing and comparison of the deduced amino acid sequence to that of native ricin A. Similarly, another plasmid, designated pRAP229, has been deposited with the ATCC on Mar. 8, 1985, with the Accession No. 53403, under the Budapest Treaty. Ricin A protein produced by *E. coli* transformed with the pRAP229 plasmid was used in the construction of the immunoconjugate in this patent application. Ricin A protein produced by *E. coli* transformed with the pRAP229 plasmid was in soluble form and associated with the intercellular environment. Besides showing proper molecular weight and immunoreactivity by Western blot and enzymatic activity, the ricin A derived from the pRAP229 transformants was shown to be cytotoxic both in vitro and in vivo. Recombinantly produced diphtheria toxin A chain and non-binding active fragments thereof are described in U.S. patent application Ser. No. 578,122 issued on May 16, 1989 as U.S. Pat. No. 4,830,962, and 648,259 issued on Jan. 16, 1990, as U.S. Pat. No. 4,894,443 which are herein incorporated by reference and are assigned to the assignee of the present invention.

When used in vivo for therapy, the toxin conjugates are, administered to the patient in therapeutically effective amounts i.e., amounts that eliminate or reduce or retard the increase of the hyperproliferating cells. The toxin conjugate will normally be administered parenterally, topically or intracavitarily. It is preferred that the administration will be local, for example, topically, ophthalmicaly or intracavitarily in the eye. The dose and dosage regimen will depend upon the name of the hyperproliferative disorder or the population of hyperproliferative cells, the characteristics of the particular toxin conjugate patient, and the patient's history. The amount of immunotoxin administered will typically be in the range of about 0.01 to about 100 mg/kg and preferably between 0.01 mg/kg and 10 mg/kg of patient weight.

The invention will be better understood in connection with the following examples which are intended by the inventor to be exemplary only and not limiting.

EXAMPLE I

Production of 454A12 and Soluble Recombinant Ricin Toxin A Chain

An anti-transferrin receptor monoclonal antibody 454A12, (454A12 MAB) was made in accordance with the description in U.S. patent application Serial No. 806,320, a continuation of which has now issued as U.S. Pat. No. 4,958,009 to Bjorn et al., which is herein incorporated by reference. The 454A12 hybridoma was deposited with the American Type Culture Collection (ATCC), Rockville, Md. U.S.A. under the terms of the Budapest Treaty and assigned Accession No. HB 10804. This antibody binds to a 95 K dalton antigen identified as transferrin receptor, but does not block binding of transferrin to the receptor.

Soluble recombinant ricin Toxin A chain can be produced using those methods described above.

EXAMPLE IA

SPDP Conjugation of RTA to the Monoclonal Antibodies

SPDP (20 mM in ethanol) was added in a 20-fold molar excess to antibody and following a 30 min incubation at room temperature, the unreacted SPDP was removed by dialysis against PBS. The extent of derivatization was determined by measuring the release of pyridine-2-thione at 343 nm after reduction with dithiothreitol (DTT). Depending on the antibody, three to eight lysine amino acid groups (per antibody molecule) were converted to the pyridyl-disulfide derivative.

The SPDP-treated antibodies were conjugated with RTA. Immediately prior to conjugation, the RTA was reduced with 50 mM DTT, then desalted on a column of chromatographic resin containing agarose, dextran and/or acrylamide to remove DTT from protein. Reduced RTA was added in a three- to five-fold molar excess over pyridyl-disulfide antibody. A typical reaction mixture (1 ml) consisted of 7 µM antibody and 30 µm RTA. The reaction was allowed to proceed overnight at 4° C. The extent of conjugation of RTA to antibody was determined spectrophotometrically by measuring the release of pyridine-2-thione. On the average, conjugates contained two to three RTA molecules per antibody molecule. This was confirmed by non-reducing SDS-PAGE gels (7.5%), which also revealed that the typical conjugate preparation contained 10%–30% free antibody.

The conjugate mixture was chromatographed on a HPLC size exclusion column to separate conjugates from residual unreacted RTA. The column was equilibrated in 0.1 sodium sulfate/0.02M sodium phosphate pH 6.8. Conjugate mixture (0.7 ml) was injected, then chromatographed at a flow rate of 1 ml/min (room temperature). Fractions of 0.5 ml were collected and the peak conjugate fractions were pooled and filter sterilized prior to cytotoxicity testing.

EXAMPLE IB

Iminothiolane Conjugation of RTA to the Monoclonal Antibodies

Figure 3:
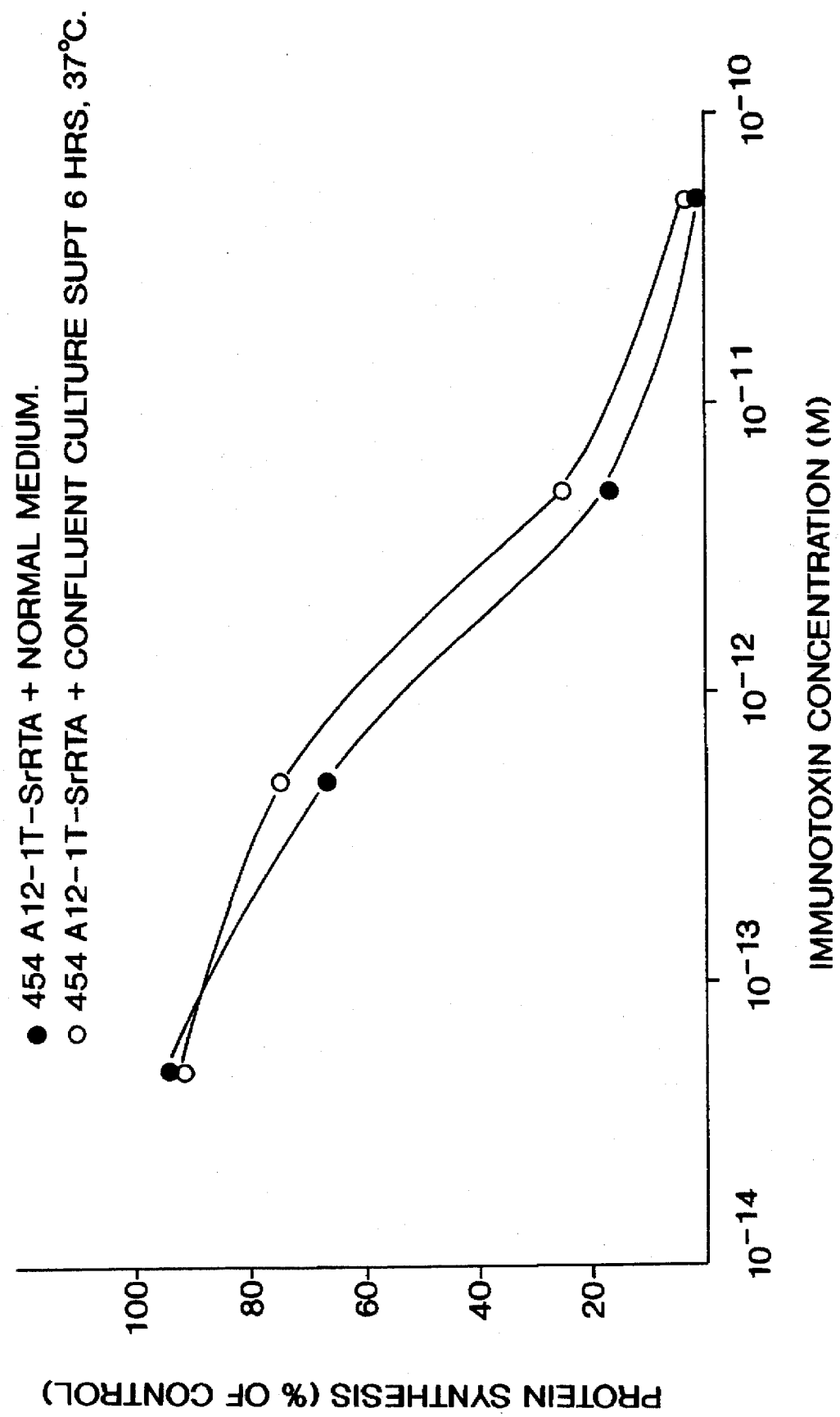
FIG. 3 is a protein synthesis assay curve of HSB2 T-lymphoblastic leukemia cells treated with varying concentrations of the anti-transferrin monoclonal antibody linked to recombinant ricin toxin A chain preincubated in medium or in a confluent culture medium supernatant for six hours at 37° C. prior to use.
Figure 4:
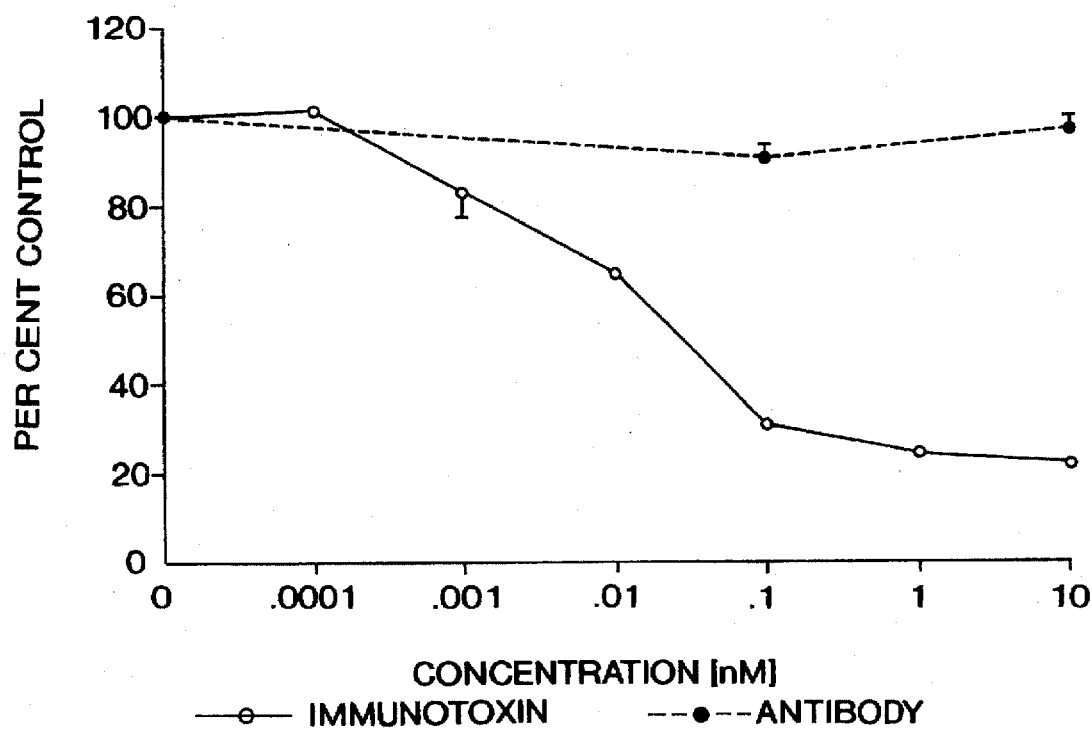
FIG. 4 shows that 454A12 MAB-rRA immunotoxin inhibits the incorporation of [$^{35}$S]methionine into proteins of sub-confluent RPE cells and the unconjugated free 454A12 MAB-rRA does not.
Figure 5:
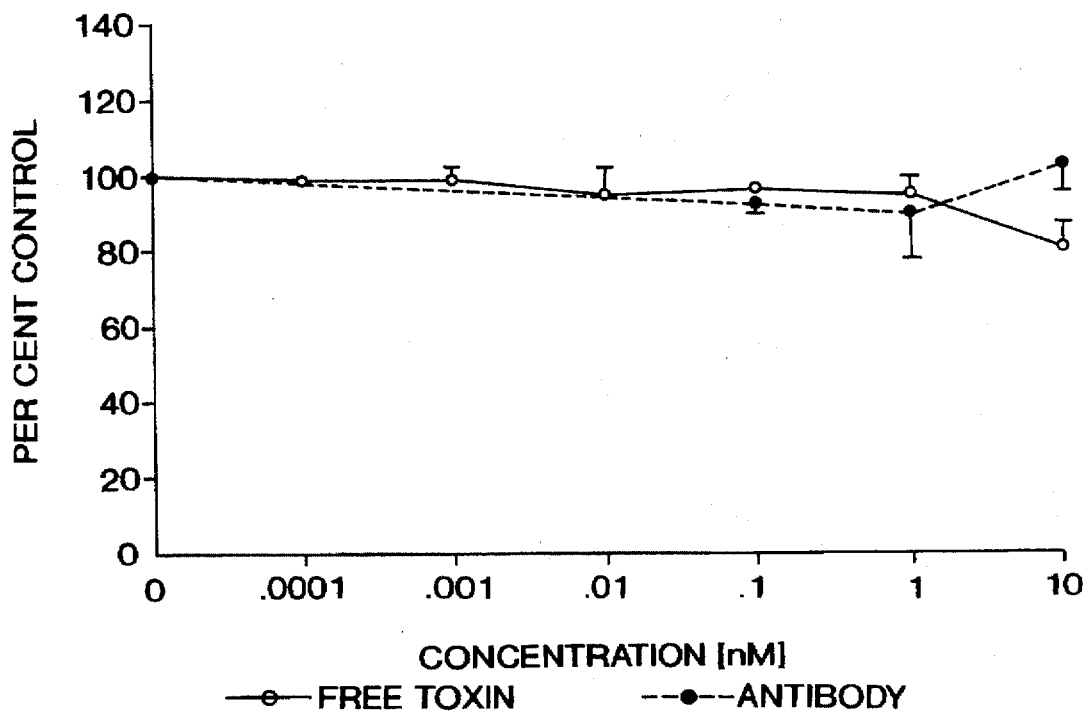
FIG. 5 shows that unconjugated recombinant ricin A chain or unconjugated free 454A12 MAB does not inhibit incorporation of [$^{35}$S]methionine into proteins of sub-confluent RPE cells. Proliferating RPE cells were incubated with unconjugated ricin A chain (rRA) or free antibody and protein synthesis measured 18 hours later.
Figure 6:
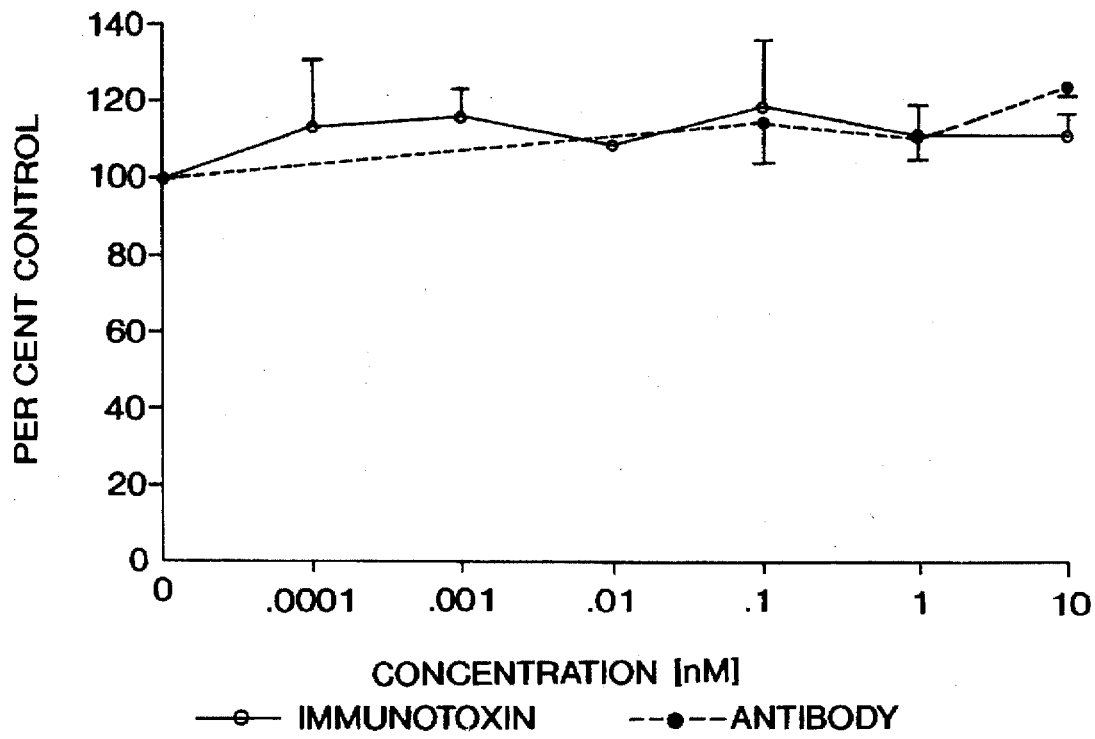
FIG. 6 shows the effect of immunotoxin on the incorporation of [$^{35}$S]methionine into proteins of confluent RPE cells. Cells were grown until proliferation ceased. They were then incubated for 4 hours with immunotoxin or unconjugated antibody and incorporation of [$^{35}$S]methionine into protein measured. Confluent RPE cells were resistant to the immunotoxin and the free antibody.
Figure 7:
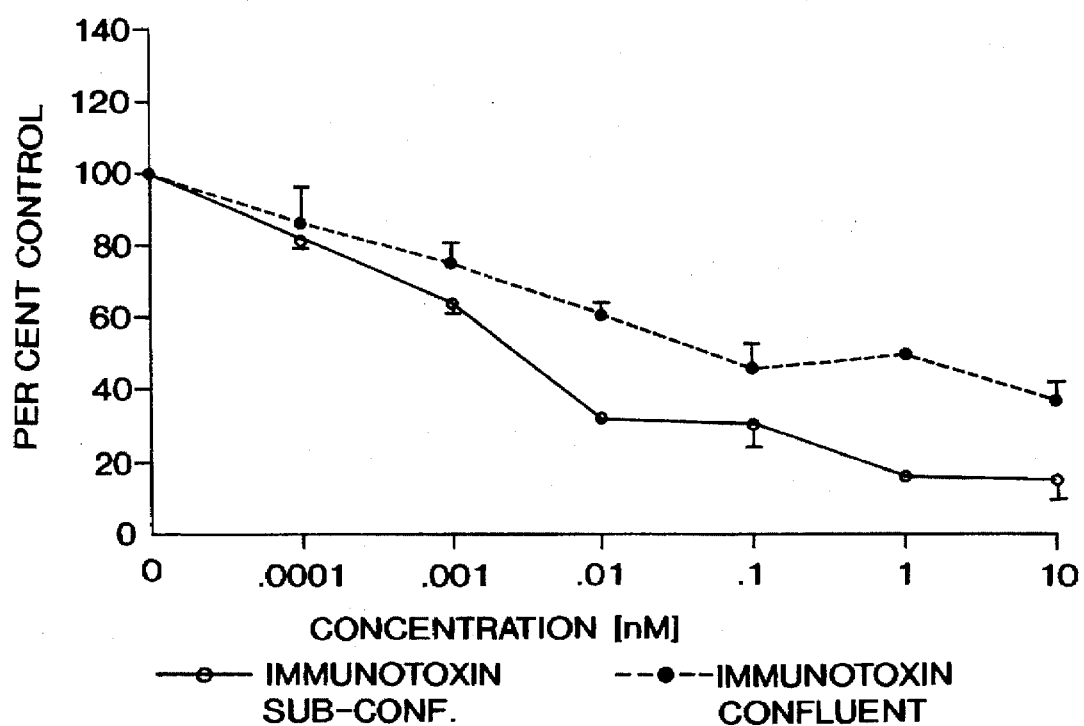
FIG. 7 shows the effect of immunotoxin on the incorporation of [$^{35}$S]methionine into proteins of sub-confluent and confluent RPE cells from a different donor. Sub-confluent and confluent cells from a different donor than those used in experiments shown in FIGS. 4–6 were incubated with various concentrations of immunotoxin for 4 hours and then incubated for 18 hours without immunotoxin. Incorporation of [$^{35}$S]methionine into protein was measured.
Figure 8:
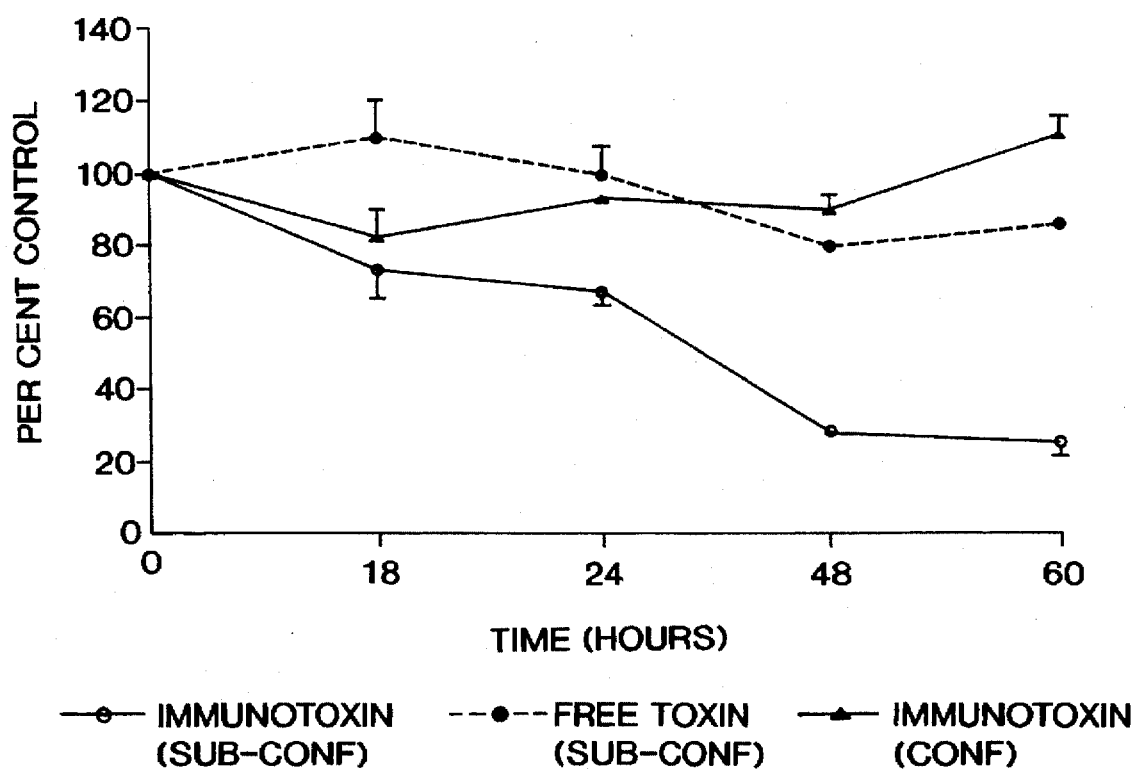
FIG. 8 shows the effect of prolonged incubation of RPE cells with immunotoxin. Proliferating or confluent RPE cells were incubated from 0.001 nM immunotoxin (454A12 MAB-rRA) or free toxin (rRA) for various periods of time. The cells were then labelled with [$^{35}$S]methionine and incorporation of radiolabel into protein measured. Subconfluent cells were sensitive to the immunotoxin and not sensitive to free rRA. The confluent cells were not sensitive to the immunotoxin.

Approximately 30 mg/ml antibody in 0.10M Na phosphate, 0.001M Na EDTA, pH 8.0 (hereafter referred to as P-EDTA buffer) is reacted with 1 mM 5,5'-dithiobis-(2-nitrobenzoic acid) (DTNB) at room temperature for about 15 min and then chilled to 0° C. in an ice bath. Enough IT is added to this solution to give an average of 2.5 IT molecules/antibody molecule, and the resulting solution is dialyzed at 0°–5° C. against three 100-fold excess volumes of P-EDTA buffer.

RTA, normally stored in P-EDTA containing 1 mM DTF, is ultra-filtered to a concentration between 10 and 15 mg/ml and dialyzed at 0°–5° C. against three 100-fold excess volumes of P-EDTA. Enough RTA is added to the derivatized antibody to give an average of 1.0–1.2 free thiols on RTA per blocked thiol on derivatized antibody. This mixture is incubated at room temperature for 2 hours.

The coupling reaction mixture is applied to a column of a chromatographic resin based on a blue dye (trysacryl blue) covalently coupled to a solid support, which mixture is then eluted with P-EDTA at room temperature. The column is scaled to contain approximately 2 ml of bed volume per mg of starting antibody. After an initial peak of unconjugated antibody has been eluted from the column, the eluant is switched to P-EDTA containing 1M NaCl. Immunoconjugate and unreacted RTA are eluted in this buffer as a very sharp peak, which is pooled and dialyzed at 0°–5° C. against one 10-fold excess volume of 0.15M Na phosphate, pH 7.1 (hereafter referred to as $p_i$ buffer). The dialyzed protein is applied to a column of a size-exclusion gel at 0°–5° C. and eluted with buffer at a flow rate of 6 cm/hr. The column is scaled to contain at least 25 ml of bed volume/ml of applied protein. Immunoconjugate is eluted as a single peak, slightly after the excluded volume, baseline-resolved from following peaks of dimerized and monomeric RTA. The pooled immunoconjugate peak is ultra-filtered at 35 psi to a final concentration of 5.0 mg/ml and filter-sterilized.

EXAMPLE II

Human corneal endothelial cell cultures were obtained from J. Polansky, Ph.D. of the University of California at San Francisco. The cells were grown in plastic tissue culture flasks (Falcon) in M199 medium (Irving Scientific, Santa Anna, Calif.), supplemented to the indicated final concentration with 20% fetal bovine serum (Flow Laboratories), penicillin 100 U/ml, streptomycin 10 μg/ml, fungizone 0.25 μg/ml (Irvine Scientific, Santa Anna, Calif.) and glutamine 2.0 mM. Cells were harvested by mild trypsinization with 0.2 ml saline containing trypsin and versine-EDTA STV for 20 minutes at 37° C. and were washed with 1.0 ml fresh medium. The cells were centrifuged at 700 xg for five minutes and were resuspended in fresh medium supplemented as above. Seed cultures containing approximately $2\times10^4$ of the cells in 0.5 ml of fresh medium were placed in sterile glass scintillation vials (2×5 cm) and were grown in a 5% CO2 atmosphere at 37° C. On days 3, 6 and 11 after seeding, immunotoxin made as described in Example IB was added to each cell culture in a volume of 50 μl to a final concentration of between $1\times10^{-11}$ M (1.8 ng/ml) and $5\times10^{-9}$M (900 ng/ml). At the time of immunotoxin addition, only the 11 day old culture had reached confluency. The cells were maintained under the above-mentioned conditions during treatment for 7 days. Seven days after addition of the immunotoxin, the culture medium was collected and the vials were washed twice with phosphate buffered saline at pH 7. The cells were trypsinized with 0.2 ml STV for two minutes at 37° C. The cells were diluted in 1.0 ml fresh medium and centrifuged at 700 xg to remove the trypsin, and resuspended in 100 μl fresh medium. An equal volume of trypan blue (Sigma) was added and viable cell counts were determined by dye exclusion. The results are reported as survival curves in FIG. 1. Values are the means of duplicate cultures.

Cells surviving in the 3 and 6 day non-confluent cultures were enlarged and irregularly shaped. FIG. 2A is a photomicrograph of the 6 day non-confluent culture 7 days after treatment with the toxin conjugate. The surviving cells of the 11 day confluent culture were tightly packed and regular in morphology. FIG. 2B is a photomicrograph of the 11 day confluent culture 7 days after treatment with the toxin conjugate. FIG. 2C is a photomicrograph of an 18 day confluent culture that was not treated with the toxin conjugate. The cell morphology is the same as the treated 11 day confluent culture.

EXAMPLE III

To show that the lack of toxic effect of the toxin conjugate was not due to inactivation of the toxin conjugate by proteases or other factors secreted by the confluent non-proliferating cells, a protein synthesis inhibition assay was carried out using HSB-2 cells as indicator cells and the immunoconjugate preincubated with the confluent culture supernatant or with fresh cell culture medium.

Twenty-five μl (5 NM) of immunoconjugate of Example I was placed in 225 μl of fresh RPM1-1640 medium with 20% fetal calf serum or 225 μl of a supernatant of the 11 day confluent corneal epithelial culture. The two test solutions were incubated for six hours at 37° C. and were serially diluted and assayed for biological activities indicated by the inhibition of protein synthesis determined from $^3$H leucine incorporation using cultures of HSB2 cells as described in Rama Krishman, S. *Science,* 223:58–61 (1984).

The results shown in FIG. 3 indicate that the efficacy of the toxin conjugate is unimpaired by the confluent culture supernatant.

EXAMPLE IV

Figure 9:
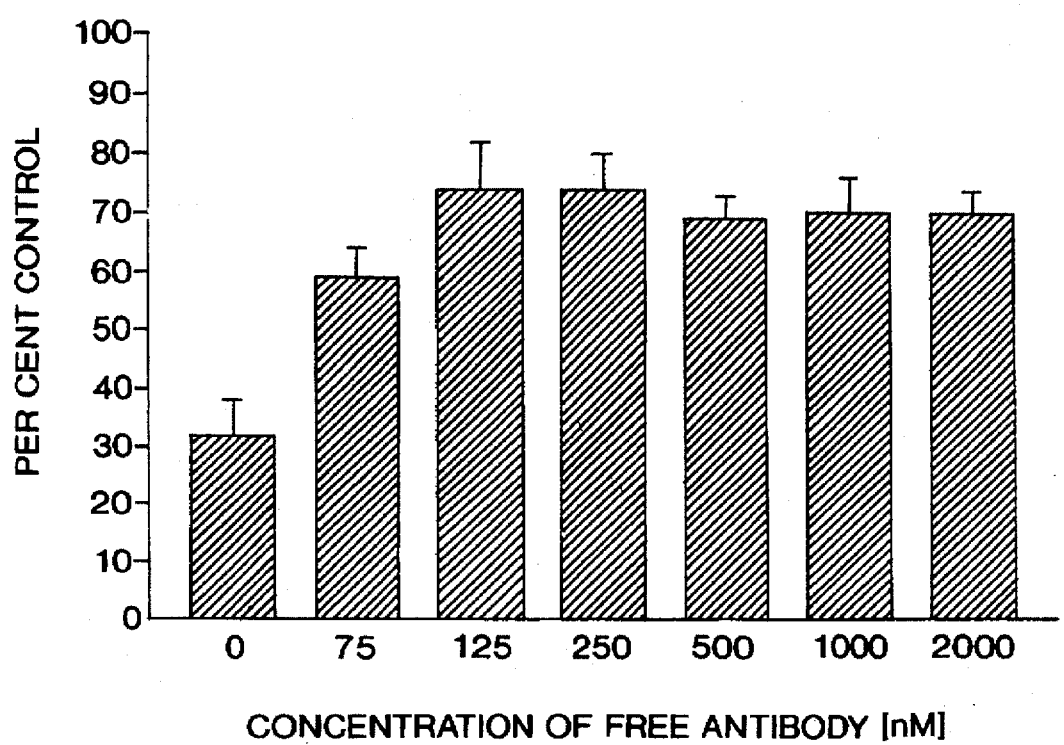
FIG. 9 shows that free antibody inhibits the cytotoxic effect of immunotoxin.

Effect of the Immunotoxin on Retinal Pigment Epithelial (RPE) Cells

The immunotoxin 454A12 MAB-rRA comprising 454A12 MAB conjugated to recombinant ricin A chain (rRA) could be used to treat pathological proliferation of fibroblasts including retinal pigment epithelia (RPE) cells. The following studies showed that in vitro, the 454A12 MAB-rRA immunotoxin inhibited protein synthesis in actively dividing (sub-confluent) RPE cells, but had a smaller or no effect on protein synthesis of confluent, non-dividing RPE cells. As shown in the following studies, the effect was specific in that neither the free ricin A chain toxin (rRA) nor the monoclonal antibody (454A12 MAB) alone had any inhibitory effect. It was also observed that the antibody competed with the immunotoxin and suppressed the latter's toxicity.

The above is demonstrated in the following four experiments.

Experiment (a) indicated the immunotoxin inhibited protein synthesis of RPE cells in a dose dependent manner. Additionally, the data suggested that the rRA and antibody must be part of a covalent conjugate for inhibition to occur. The immunotoxin exerted no effect on non-proliferating cells. Confluent cells showed some inhibition. However, the inhibition was substantially less than that found in growing cells.

Experiment (b) indicated that the immunotoxin exerted greater inhibitory effect on proliferating RPE cells after prolonged incubation with the cells. However, the immunotoxin had little effect on confluent cells even after prolonged incubation.

Experiment (c) showed that the five antibody competed with and reduced the inhibitory effect of the immunotoxin on sub-confluent RPE cells.

Experiment (d) showed that the transferrin receptor density decreased as the PRE cells ceased proliferation.

Details of experiments (a) through (d) follow:

A. Inhibition Of RPE Cell Protein Synthesis by Immunotoxin

RPE cells were isolated from human donor eyes and grown on laminin-coated tissue culture dishes by techniques known in the art. Cultures were inspected to determine the degree of confluence and the cell number was determined by trypsinization and counting on a hemocytometer. The rate of cell growth differed between the donors.

RPE cells were grown to semi-confluence (approximately $1.4\times10^5$ cells per plate) in fresh medium and incubated with various concentrations of immunotoxin (454A12 MAB-rRA), antibody (454A12 MAB) or recombinant ricin A chain (rRA) that had been diluted into the medium. The cells were incubated for 4 hours at 37° C. Then the cells were washed free of immunotoxin, antibody or rRA, and incubated in supplemented F-10 medium for a further 18 hours. They were rinsed again in methionine-free minimal essential medium (Flow Labs, 7655 Old Springhouse Road, McClean, Va. 22102) and incubated for 1 hour in medium with [$^{35}$S]methionine (Amersham Corp., 2636 South Clearbrook Drive, Arlington Heights, Ill. 60005) to measure the rate of protein synthesis.

Incorporation of labelled amino acid into protein was measured by trichloroacetic acid precipitation: the cells were rinsed in phosphate buffered saline (PBS) and 10% trichloroacetic acid was added. The cell precipitate was filtered through Millipore filters, washed and the incorporated radioactivity determined by scintillation counting. In additional experiments, a similar procedure was used except that the time of exposure of the cells to the immunotoxin, antibody or ricin A chain was increased. The rate of incorporation of radiolabel was expressed relative to that by cells that had been treated in the same manner except that they had received no exposure to immunotoxin.

FIG. 4 shows that there was a dose dependent inhibition of cell protein synthesis after pre-incubation with immunotoxin. No such effect was seen when anti-transferrin receptor antibody alone was incubated with the cells instead of the immunotoxin, suggesting that the antibody itself was not the cause of the inhibitory effect (FIG. 4). No inhibitory effect was observed in similar experiments in which unconjugated ricin A chain, instead of the immunotoxin was incubated with the cells (FIG. 5). These data, therefore, show that for inhibition to occur, rRA and antibody must be part of a covalent conjugate. The data illustrated in FIGS. 4 and 5 are representative of three similar experiments.

Similar incubations with various concentrations of immunotoxin, free rRA and free antibody were carried out with cells that had grown to confluence (approximately $5.7\times10^5$ cells per plate). These cells still incorporated [$^{35}$S] methionine into cellular proteins as part of their protein mover functions though cell number no longer increased. FIGS. 6 and 7 show the results of two of these experiments. In FIG. 6, no effect of the immunotoxin or free antibody was apparent after pre-incubation of either with non-proliferating cells. Confluent cells from another set of donors also showed inhibition by immunotoxin, but to a lesser degree; an example of this is shown in FIG. 7. Additionally, it was found that as with sub-confluent cells, free toxin had no effect on confluent cells (not shown).

B. Effect of Prolonged Incubation with Immunotoxin on Protein Synthesis by RPE Cells In the experiments described in the preceding section, the cells were exposed to immunotoxin for 4 hours. In the experiment illustrated in FIG. 4, there was an approximately 25% reduction in incorporation of radiolabel using a concentration of 0.001 nM immunotoxin. In order to determine whether a greater effect would be seen at longer periods of incubation, cells were incubated with this concentration of immunotoxin for up to 60 hours. FIG. 8 shows that indeed there was a greater effect over a longer period of exposure of 0.001 nM immunotoxin so that by 60 hours of incubation, incorporation of [$^{35}$S]methionine was reduced by 80%. In these experiments a small effect of the free toxin was seen, in some cases, after long periods of incubation. In contrast to the results with sub-confluent cells, even 60 hours of incubation with the immunotoxin had little effect on confluent cells (FIG. 8).

C. Effect of Competing Free Antibody on Protein Synthesis Inhibition by Immunotoxin Substantial (up to 80%) inhibition of protein synthesis was observed in sub-confluent RPE cells after incubation with 10 nM immunotoxin for 4 hours (FIG. 4). This appeared to be an effect specific to the immunotoxin because free antibody or rRA had no effect. If the toxicity was caused by recognition of the transferrin receptor by the immunotoxin, then free antibody should compete with the immunotoxin for transferrin receptors and reduce the inhibitory effect. To determine whether this was the case, cells were incubated for 4 hours with 10 nM immunotoxin or the same concentration of immunotoxin plus competing antibody at concentrations of 75 to 2000 nM. The cells were then returned to normal medium for a further 18 hours. 10 nM immunotoxin reduced incorporation of [$^{35}$S]methionine to about 32% of control values (for untreated cells). Competing antibody, up to 2 µM, clearly inhibited the effect of the immunotoxin (FIG. 9), though its effect was never completely abolished.

D. Alterations in the Number of Transferrin Receptors on RPE Cells During Proliferation The finding that sub-confluent RPE cells are sensitive to immunotoxin, but in most cases confluent cells are not, is most easily explained by the known reduction in transferrin receptor density as cells cease proliferation. In this experiment, diferric was radioiodinated using Iodogen (Fierce Chemical Co., P.O. Box 117, Rockford, Ill. 61105) and Na$^{125}$I (Amersham Corp., supra). Transferrin binding was measured by first growing cells in culture for 24, 48 and 60 hours and then incubating them with saturating amounts, determined from preliminary experiments, of $^{125}$I-labelled transferrin. At 24 hours, the cells were sub-confluent, while at 48 and 60 hours, proliferation had ceased. Nonspecific binding was determined in duplicate incubations containing excess unlabelled transferrin.

Figure 10:
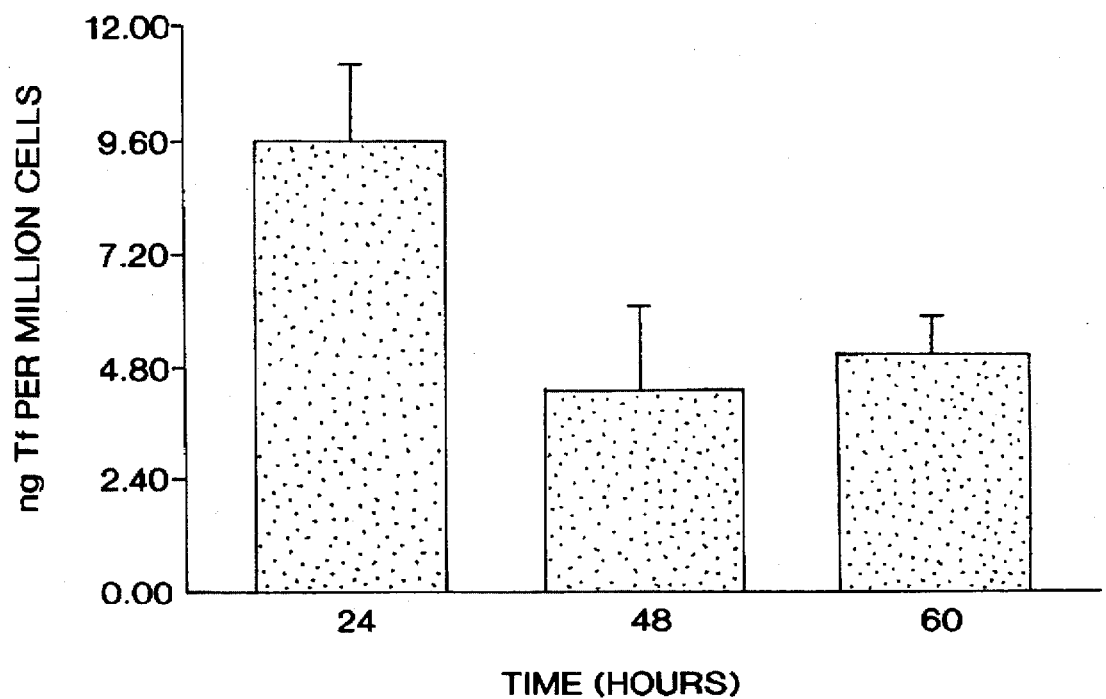
FIG. 10 shows the changes that transferrin receptor levels on RPE cells decrease with time in culture.

It was observed that at 24 hours the average transferrin binding was equivalent to approximately 72,000 binding sites per cell. At confluence (48 hours) this fell to 35,000 binding sites per cell, but did not fall further as the culture became older (FIG. 10). Although confluent cells become refractory to the immunotoxin, as judged by their continued protein synthesis at rates similar to control cells, they do not lack transferrin binding sites.

EXAMPLE V

Effect of the Immunotoxin 454A12 MAB-rRNA On Human Corneal Endothelial Cells

The following experiments were carried out to determine the effect of the immunotoxin 454A12 MAB-rRA on human eye tissue. The experimental data suggested that in order to inhibit the growth of human corneal endothelial cells, the cells must be proliferating and the ricin A chain must be conjugated to the antibody. Uncoupled ricin A chain or antibody had minimal inhibitory effect on the growth of proliferating cells. The details of the experiment is as follows:

A. Materials

Human corneal endothelial cells were used. The immunotoxin consisted of recombinant ricin A chain (rRA) chemically linked by iminothiolane (IT) to a monoclonal antibody (MAB).

Additionally, to show the requirement for coupling between the transferrin receptor antibody and the ricin A chain, the effects of 454A12 MAB-rRA were compared to the unconjugated 454A12 monoclonal antibody, ricin A chain (rRA), and MOPC21-IT-rRA, a non-specific immunoglobulin IgG$_1$-recombinant ricin A chain complex.

B. Method

1. Source and Maintenance of Corneal Endothelial Cells

Under sterile conditions, human corneal endothelial cells were scraped from donor corneas within two hours of harvesting. Stock cultures were seeded on gelatinized 35 mm dishes in medium 199 containing 15% fetal calf serum, Earl's balanced salts, and 1% of 200 mM glutamine. The cells were maintained in 5% CO$_2$ at 37° C. with fibroblast growth factor added every other day. Once confluent, cells were trypsinized and seeded in 2 mL of medium on gelatinized 35 mm dishes at 2×10$^4$ cells/mL for individual experiments.

2. Assay of Immunotoxin Activity

The effect of 454A12 MAB-rRA on cellular proliferation was assayed in duplicate using serial dilutions of immunotoxins. Four sets of controls were used: plates without additives; with unconjugated rRA; with purified, unconjugated 454A12 antibody; and with ricin A chain conjugated to MOPC21, a non-specific immunoglobulin IgG$_1$. Proliferating cells were exposed continuously to a single dose of 454A12 MAB-rRA or control protein for all 7 days of culture, whereas confluent cultures were exposed for 7 days after achieving confluence. Dead cells were observed to detach from dishes and were removed prior to counting; unexposed plates did not contain detached, nonviable cells. No detached cells were viable as assessed by trypan blue exclusion. The number of live cells was determined with a Coulter counter.

The effect of immunotoxin on amino acid incorporation (a measure of persistent ribosomal function and cell viability) was assayed using cells which had been seeded with 3×10$^4$ cells in 0.5 mL of medium in borosilicate glass vials coated with 0.2% gelatin. After 48 hours of proliferation, cells were incubated in duplicate for 18 hours in the presence of 454A 12 MAB-rRA. Cells were then rinsed three times with phosphate buffered saline (PBS) and incubated with 0.2 mL of leucine free 1640 RPMI containing 2.0 µC$_1$ of $^3$H-leucine. Fetal calf serum (10%) was added to maintain cellular adherence during the incubation with $^3$H-leucine. After 3 hours of incubation, the cells were washed three times with PBS and the protein was precipitated with 5% trichloroacetic acid. Counts were measured in a Tricarb® liquid spectrometer scintillation counter with 5 mL of scintillation fluid.

3. Data Analysis

The effects of 454A12 MAB-rRA on cellular proliferation and $^3$H-leucine incorporation were determined by comparing the growth or incorporation in plates or vials from the same stock to which no 454A12 MAB-rRA was added. Results without additives, defined as representing 100%, served as controls for that experiment, and were compared to results of cultures treated with 454A12 MAB-rRA, rRA, or 454A12 alone. Percent cell survival and $^3$H-leucine incorporation for all additions were calculated and compared to controls. These data were plotted against the log dose (ng/mL) of 454A12 MAB-rRA.

C. Results

Figure 11:
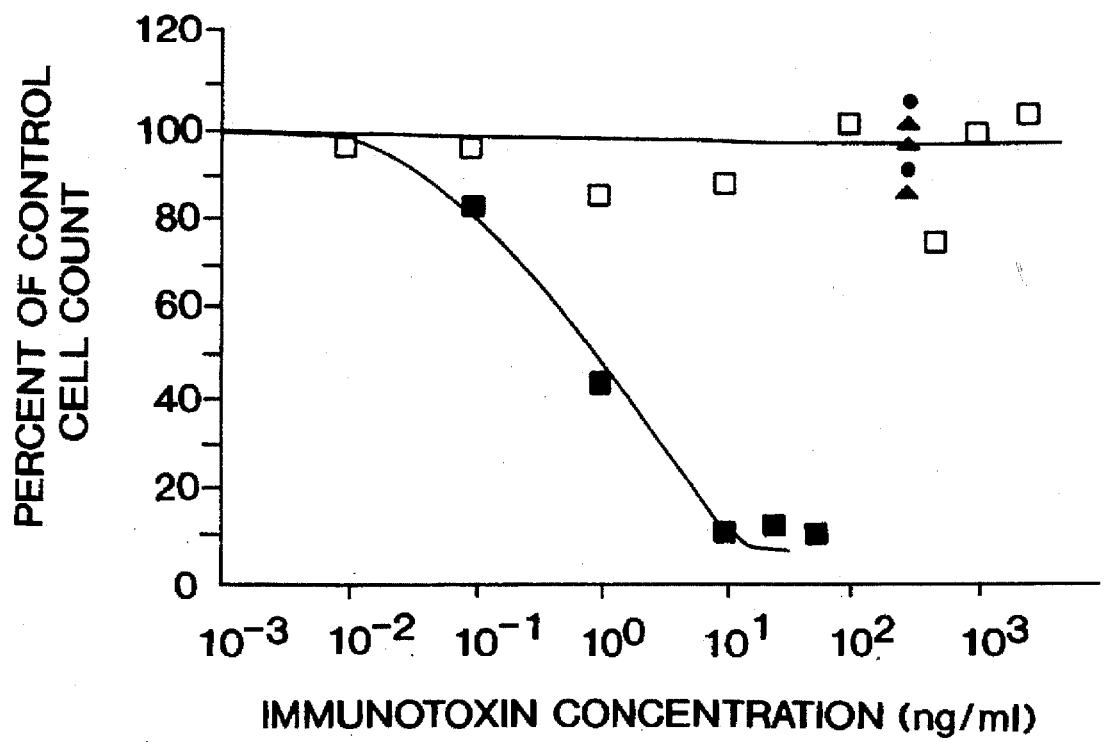
FIG. 11 shows the effect of different doses of 454A12 MAB-rRA on confluent and proliferating human corneal endothelium (HCE) cells. Confluent HCE cells are not sensitive to the immunotoxin, but subconfluent cells are sensitive.
Figure 12:
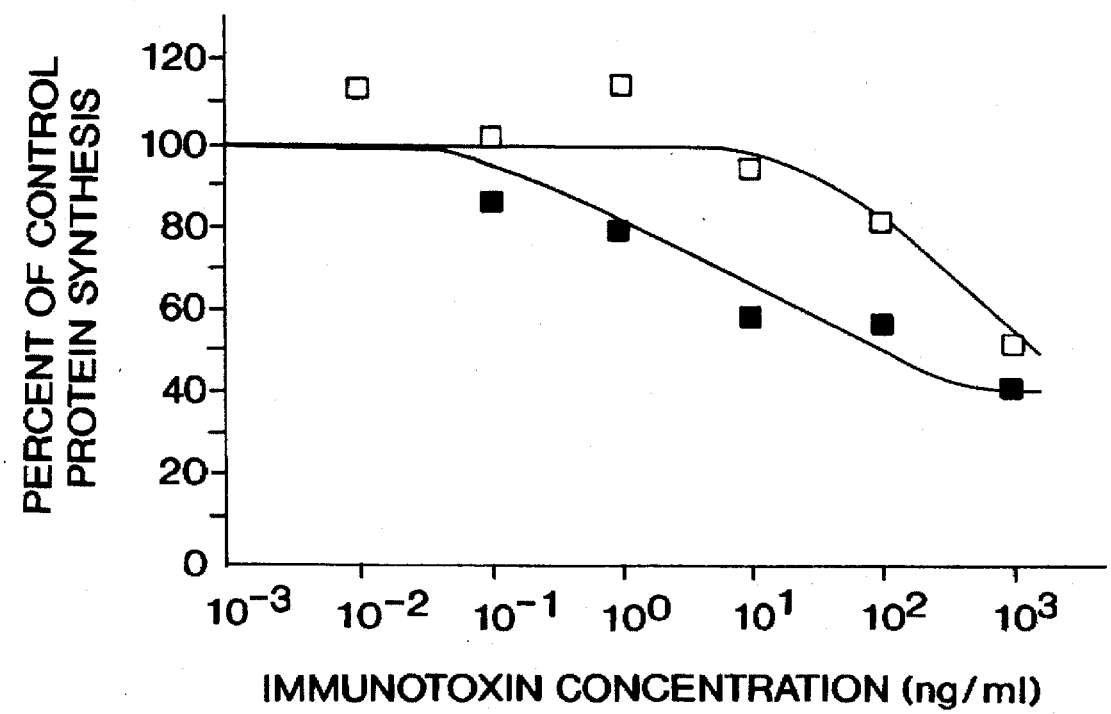
FIG. 12 presents the percentage of protein synthesis for confluent and proliferating HCE, compared to unexposed controls, at different concentrations of 454A12 MAB-rRA. Confluent HCE cells are not sensitive to the immunotoxin, but subconfluent cells are sensitive.

The results (FIG. 11) showed that immunotoxin 454A12 MAB-rRA significantly inhibited proliferating human corneal endothelium (HCE) in a dose dependent fashion. A concentration of 50 ng/ml of the immunotoxin caused an 89% decrease in the number of viable cells. Protein synthesis was inhibited by immunotoxin in both proliferating and non-proliferating cells but less effectively in the latter. (FIG. 12) The concentration of immunotoxin which produced 50% inhibition of cell growth (IC$_{50}$) was calculated to be 100 ng/ml for proliferating cells but 1000 ng/ml for confluent cells.

In contrast to its effect on proliferating cells, the immunotoxin had no significant effect on confluent cells even at doses as high as 2500 ng/ml. (FIG. 11) No significant effect on growth of proliferating cells were exhibited by unconjugated 454A12 or free ricin A chain. On the other hand, MOPC21-IT-rRA inhibited cell growth by 25% at 250 ng/ml.

EXAMPLE VI

Inhibition of Fibroblast Growth In Vitro in a Simulated-Vitreous Medium by the Immunotoxin 454A12 MAB-rRA To determine if the immunotoxin 454A12 MAB-rRA could inhibit fibroblasts growing in the vitreous, experiments were carried out on the inhibition of fibroblast proliferation in a three dimensional, hydrated collagen model which simulates the vitreous of the eye. The experiments were carried out as follows:

A. Method

The procedure followed was essentially that of Van Bockxmeer, F. M., et al., 1982, *J. Tissue Culture Methods*, 7:163–167, "Measurement of Cell Proliferation and Cell Mediated Contraction in 3-Dimensional Hydrated Collagen Matrices".

1. Preparation of Sterile, Stable Collagen Solutions

Amputated rat tails were soaked in 70% ethanol in water for 2 hours after which the skin was reflected. The tails were sectioned into 3 cm segments which were placed in 70% ethanol/$H_2O$ for 1 hour then washed three times with 70% ethanol.

Using a laminar flow hood and sterile techniques, the ethanol solution was decanted and replaced with an equal volume of sterile, normal saline for 90 minutes. The tail segments were squeezed at their mid-point to induce extrusion of tendons from the cut ends. The tendons were washed twice with normal saline and placed into glacial acetic acid solution (1 part glacial acetic acid in 1000 parts distilled water) with a magnetic stirring bar. The solution was stirred in a sealed container at 4°–6° C. for 48 to 72 hours, after which the suspension was decanted into sterilized centrifuge tubes and spun at 25000 x g for 2 hours at 4° C. The sterile collagen solution (supernatant) was transferred to sterile polypropylene robes, and the protein concentration was adjusted to 1.4 mg/mL (Kjeldahl method). The collagen solution was then tested for its ability to form a mechanically stable gel within 20 seconds at 37° C. (only such solutions were used in the described experiments). The collagen solution was stored at −76° C. or in liquid nitrogen.

2. Cell Suspensions

Using aseptic technique, confluent human foreskin fibroblast cell cultures were treated with trypsin to separate the cells, washed, counted, suspended to the appropriate concentration and stored on ice until the collagen gel was prepared. The level of cell viability was verified by trypan blue exclusion.

3. Test for Gelling Capacity of Collagen

The collagen solution was thawed and all reagents and robes were cooled to 4° C. To 1500 µL collagen solution was added 600 µL 5 x RPMI 1640, 300 µL FBS, 100 µL 0.4M NaOH, 107 µL 5.6% $NaHCO_3$, 30 µL 200 mM L-glutamine, 30 µL penicillin (5000 U/mL)/streptomycin (5000 µg/mL) and 335 µL distilled $H_2O$. The robe was capped, the contents rapidly mixed, placed in a 37° C. water bath, and gently tilted to 60° relative to the vertical at 15 second intervals. Gelling was noted. The gel was destroyed with a glass rod and the pH was measured. If the pH was not 7.4, it was adjusted by adding NaOH to the reaction mixture. If the collagen did not gel within 5 minutes, either the pH required further adjustment or the collagen solution was old and therefore not used.

4. Imbedding of Cells in Collagen Gels

All reagents and plastic robes were prechilled to 4° C. in an ice bath. Cells which had been preincubated with various concentrations of 454A12 MAB-rRA followed by a wash were resuspended at $5 \times 10^4$ cells/100 µL, of FBS and stored on ice. A solution of the following composition was prepared: 200 µL of 5 x RPMI 1640 without glutamine or $NaHCO_3$, 36 µL 5.6% $NaHCO_3$, 33 µL 0.4M sterile NaOH, 111 µL sterile $H_2O$, 10 µL penicillin (5000 U/mL)/streptomycin (5000 µg/mL) and 10 µL L-glutamine (200 mM). The cell suspension and the solution were rapidly mixed and added to 500 gL of collagen solution yielding a solution of $5 \times 10^4$ cells/mL collagen gel containing 0.7 mg collagen/mL. A 150 µL aliquot of this gel solution was dispensed to 96-well plates. The gels were overlaid with 50 µL of RPMI growth medium with or without $^3$H thymidine (0.1 µC$_1$/well).

Samples and appropriate controls were run in quadruplicate wells. Plates were incubated for the appropriate number of days (4–20) at 37° C.

5. Cell Harvesting for Thymidine Counting

Using aseptic techniques, the gel was overlaid with 50 µL of an aqueous solution of 15 mg collagenase and 0.625 mL Triton per 100 mL water, and the plate was incubated for 3 hours at 37° C. Cells were harvested with a Cambridge Technology PHD Model 200 A automated cell harvester using a distilled water rinse. Each filter section was placed into a counting vial to which 4 mL of Aquasol® was added, vortexed, allowed to stand for 30 minutes, and counted for 5 minutes in a scintillation counter.

B. Results

The results indicated that greater than 50% inhibition of thymidine uptake was seen after 60 minutes of incubation with 100 ng/ml of 454A12 MAB-rRA whether the cells were cultured for 4 or 20 days. (Table 3) At higher doses (500–2000 ng/ml) greater than 70% inhibition was observed after both culturing periods. The data indicate that 20 min exposure to 500 ng/ml of 454A12 MAB-rRA was sufficient to inhibit growth for 20 days. Higher doses required shorter periods of immunotoxin exposure for the same degree of inhibition. The brevity of the exposure time should minimize the toxic potential of higher doses on non-proliferating cells.

The data further indicated that the immunotoxin was effective in a gel environment similar to that found in the vitreous.

EXAMPLE VII

Comparison of the Relative Inhibitory Activities of Immunotoxin and Immunotoxin Components on the Growth of Human Fibroblasts in Culture In this study, the immunotoxin 454A12 MAB-rRA was compared for activity with ricin A chain, the monoclonal antibody 454A12, and a non-specific immunoglobulin with ricin A chain attached by a similar chemical linkage, i.e., by SPDP-disulfide linkage. All compounds were tested in the simulated vitreous medium (Example VI) used to demonstrate the activity of the immunotoxin. The study was carried out as follow:

A. Methods

The methods were similar to those described in Example VI. The substances with which the activity of immunotoxin was compared are MOPC21-IT-srRTA, sr-RA, and 454A12 MAB. MOPC21-IT-srRTA is a non-specific immunoglobulin (IgG$_1$) combined to ricin A chain which, because of its non-specificity, is frequently used as a negative control in immunotoxin studies. The compound sr-RA is soluble, recombinant ricin A chain.

B. Results

The data supported the specific toxicity of the immunotoxin 454A12 MAB-rRA in a simulated vitreous medium for cells which can internalize ricin A chain. The result (Table 4) showed that there was no significant difference between 4 and 20 days growth at 1000 ng/ml after 10 minute incubation with the compounds. Further, regardless of the duration of cell growth, inhibitor concentration, or exposure time to the drug, the maximum inhibition was a 23% inhibition by ricin A chain alone at 4000 ng/ml and 10 minute exposure compared to 76–98% inhibition by 454A12 MAB-rRA at concentrations as low as 500 ng/ml.

EXAMPLE VIII

Inhibitory Effect of Immunotoxin 454A12 MAB-rRNA on Growth of Human Fibroblasts Implanted in Rabbit Eyes The following in vivo studies showed that the immunotoxin 454A12 MAB-rRA significantly reduced the proliferation of human fibroblasts injected into the vitreous cavities of rabbits. The human fibroblasts had been incubated in rabbit eyes to simulate human vitreoretinopathy. The result strongly suggested that the immunotoxin could be effective in the prevention of vitreoretinopathy.

A. Methods

1. Preparation of Human Fibroblasts used for Intraocular Injection

Human foreskin fibroblasts were grown at 37° C. in a humidified atmosphere in RPMI medium supplemented with 10% fetal calf serum in polyethylene flasks. After 8 to 16 passages, cells were harvested by incubation with 0.25% trypsin for 5 minutes. The digestion was stopped by addition of RPMI with fetal calf serum, the cells were centrifuged at 1000 rpm for 5 minutes, then resuspended in a serum free RPMI solution, and a sample was removed for viability testing by trypan blue exclusion and counting in a hemocytometer. Cells were re-centrifuged and diluted to a final concentration of 250,000 cells/0.1 mL.

2. Rabbit Vitreous Model a) preparation of Bloodless Injection Site in the Rabbit Eye Pigmented rabbits (4.0–5.5 kg) were anesthetized with ketamine hydrochloride, acepromazine, and rumfin. A bloodless-injection area was prepared by the following sequence of steps: first by tattooing a 1.0 to 1.5 mm diameter region of the sclera located 5 to 6 mm posterior to the limbus in the anterior superior quadrant. One week later 5 or 6 applications of a Keeler Amoiles retinal cryoprobe cooled to −60° C. were made over the tattooed area. After 3 to 4 weeks, the area of cryopexy was examined with an indirect ophthalmoscope. Cryopexy was repeated if there was not a marked degree of choroidal pigment alteration. Approximately 3 weeks later, animals were anesthetized and very heavy diathermy treatment was performed through the sclera and chorioid in the center of the scleral tattoo using a conical diathermy tip. This latter step completed preparation of a bloodless-injection area.

This procedure ensured that proliferating rabbit cells would not be released at the injection site. By preventing rabbit cell proliferation, examines were better able to assess human cell proliferation.

b) Injection of Fibroblasts into the Rabbit Eye

A paracentesis was performed to remove 0.2 to 0.3 mL of aqueous from the anterior chamber. Immediately after, 500,000 human fibroblasts (suspended in 0.2 mL RPMI) were injected through the area of diathermy using a 30 gauge needle under direct observation with the indirect ophthalmoscope. The needle was positioned to inject the cells approximately 2 mm above the optic nerve and medullary rays. A second paracentesis was performed 30 minutes later and 8000 ng of 454A12 MAB-rRA in 0.1 mL RPMI was injected into one eye while the contralateral eye was injected with 0.1 mL of RPMI. Randomization of the eyes to control or treated groups was determined by the flip of a coin. Assuming a vitreous volume of approximately 2 mL for the rabbit eye, the final concentration of immunotoxin in the area was 4000 ng/ml. Each fundus was examined 30 minutes later. Evidence of bleeding at the injection site excluded the animal from the study. At two week intervals, eyes were examined and graded, according to the criteria listed in FIG. 13, by an examiner who was blinded to the history of drug injection.

B. Results and Discussion

1. Method of Statistical Analysis

The extent of inhibition in the proliferation of the human fibroblasts was determined by comparing the growth between the two eyes of each animal using the unpaired two-tailed t test.

The evaluation of the eyes is presented in Table 1, where the extent of estimated growth in each eye is represented as a ratio, (right eye value/left eye value). The criteria used to rank the amount of growth as presented in FIGS. 13 and 14, were modified from Fastenberg, D. M. et al., 1982 (a), *Am. J. Ophthalmol.*, 93:565–72, "The Role of Cellular Proliferation in an Experimental Model of Massive Periretinal Proliferation" and 1982 (b), *Am. J. Opthalmol.*, 93:559–64, "A Comparison of Different Cellular Inocula in an Exaperimental Model of Massive Periretinal Proliferation". A conclusion as to whether the growth was less or greater than the controls at the end of the experiment is also presented in the last column of Table 1. The decreased growth found in the treated eyes was statistically significant ($p<0.0001$) compared to the control.

To express these results in a more common mode of presentation, the percent inhibition by the immunotoxin relative to the control was determined by calculating the difference between the control and treated groups and expressing this difference as percent of the control, i.e., $[(C-T)/C]\times100$, for each animal at each time the eyes were examined (Table 2). Stimulation of growth was represented as a negative number. After the percent inhibition was calculated, the median inhibition was determined for each rabbit over the 12 weeks of the study. Using this method, at least 50% of the rabbits treated with the immunotoxin had inhibition of at least 62.5% whether inhibition was shown as early as the first two weeks or by a later time period.

Although the difference between rings (e.g., 1+ and 4+) is not linear, the calculation of a percent inhibition does provide a method for the overall quantitation and comparison of a large number of values.

Figure 15:
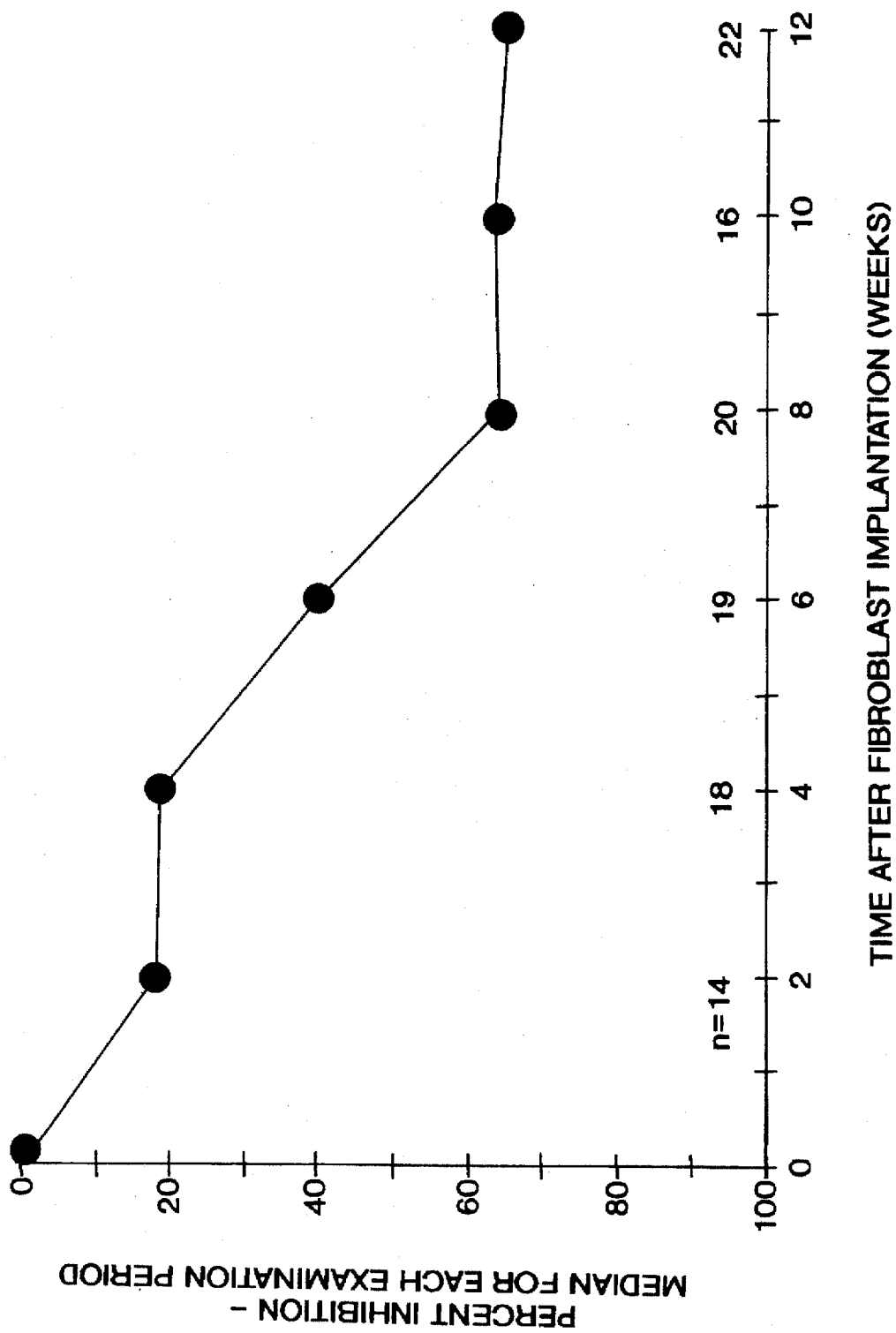
FIG. 15 presents inhibition of growth of human fibroblasts, in rabbit eyes by 454A12 MAB-rRA.

To demonstrate the effects of treatment duration, the median inhibition by the immunotoxin of all 23 rabbits was determined for each reading period, e.g., 2 weeks, 4 weeks, etc., and the results plotted against time (FIG. 15). Percent inhibition increased with time to about 8 weeks at which point it leveled off at about 65%. These values also include one animal that showed marked stimulation of growth for unknown reasons.

The inhibition of human fibroblast growth by the immunotoxin 454A12 MAB-rRA strongly suggests this compound may be effective in the prevention of vitreoretinopathy in humans.

EXAMPLE IX

Primate Toxicity of 454A12 MAB-rRA

The following studies showed no observable difference in toxicity between 454A12 MAB rRA and non-specific MOPC21 MAB-rRA in vitro studies on Rhesus and Chimpanzee cells.

A. In Vitro Studies on Rhesus and Chimpanzee Cells

In vitro cytotoxicity studies were conducted with 454A12 MAB-rRA and non-specific MOPC21 MAB-rRA control on Rhesus lung and kidney cell lines and a Chimpanzee cell line. Studies were also performed on Rhesus, PHA stimulated, peripheral blood leukocytes. No difference in cytotoxicity was observed between 454A12 MAB-rRA and control MOPC21 MAB-rRA.

Further cytotoxicity studies were conducted with 454A12 MAB-rRA and 260F9 MAB-rRA on primates in the following experiments.

B. primate Intraperitoneal Toxicity Study of454A12 MAB-rRA

Sixteen monkeys, four in each of four dosage groups, were dosed at 0 (excipient control), 1, 10, and 100 μg/kg, i.p., every other day for 4 doses. Thereafter, the monkeys were monitored for clinical and laboratory changes for a further 21 days. The animals exhibited a mild acute phase response, characterized by an increase in segmented neutrophils and fibrinogen; additionally, a decrease in serum albumin and a questionable increase in globulin were observed. No other test-article related changes were seen. All 454A12 MAB-rRA treated animals developed anti-drug antibodies, with earliest measurable antibody occurring by day 8 in some animals. Two animals were observed to have low levels of pre-existing antibody reactive with rRA. The clinical course of these animals was not significantly different from that of animals without this reactivity.

EXAMPLE X

Medical Applications

For parenteral administration, the toxin conjugate will be formulated in a unit dosage injectable form (solution, suspension, emulsion) in association with a pharmaceutically acceptable parenteral vehicle. Such vehicles are inherently nontoxic and non-therapeutic. Examples of such vehicles are water, saline, Ringer's solution, dextrose solution, and 5% human serum albumin. Nonaqueous vehicles such as fixed oils and ethyl oleate may also be used. Liposomes may be used as carriers. The vehicle may contain minor amounts of additives such as substances that enhance isotonicity and chemical stability, e.g., buffers and preservatives. The immunotoxin will typically be formulated in such vehicles at concentrations of about 0.01 mg/ml to 100 mg/ml.

It will be readily appreciated by those skilled in the art that the above-described compounds may be formulated with any one of a number of well known pharmaceutically acceptable carriers, depending upon the optimal mute of administration, e.g., topical, ophthalmic, parenteral, including intravenous, intraperitoneal, intracavitarily or intraophthalmic.

Such carriers include solutions compatible with the mode of administration and solubility of the compounds. Such solutions may be buffered or otherwise formulated to minimize undesirable localized effects of injection if necessary. Formations for administration are also well known to those skilled in this art and may be formulated for various effects, including timed, slow and delayed release. The compounds, formulated for these effects, may be administered in the form of suspensions, slurries and liquids. Such dosage forms may also include excipients, or other therapeutically inert ingredients in the formulation of the desired pharmaceutical preparation.

For parenteral use, the compounds of this invention can be formulated with sterile ingredients compounded and packaged aseptically. They may be administered intravenously or intracavitarily. Useful solvents for formulation in such use are the polyhydric aliphatic alcohols and mixtures thereof. Especially satisfactory are the pharmaceutically acceptable glycols, such as propylene glycol, and mixtures thereof. Glycerine is another example of a polyol which is a particularly convenient solvent system. A pH range, about 7.4, and isotonicity compatible with body isotonicity, is desirable. Basicity may be controlled by the addition of a base as required, and a particularly convenient base is monoethanolamine. For topical use the toxin conjugate may be formulated in an ointment, augment or highly viscous oil or cream or lotion suitable for topical use. Such suitable topical formulations are known to those skilled in the art. Topical application of the immunotoxin may be used, for example, in the treatment and prevention of pterygium, or in the prevention of scarring due to cell proliferations. To prevent regrowth of pterygium after surgery, the immunotoxin can be topically applied; injected into the afflicted site after surgery; or injected into the growing end of a small pterygium. Similar methods of applications by injection may be applied in the case of post glaucoma surgery. For topical ophthalmic use the toxin conjugate may be in the form of drops or an ointment or topical slow release gel suitable for ophthalmic application. Such suitable ophthalmic formulations are known to those skilled in the art. The percentage of the compound to be used in the pharmaceutical carrier may be varied. It is necessary that the compound constitute a proportion such that a suitable dosage will be obtained.

The dosage required to achieve the desired pharmacologic activity in the mammal will vary with various factors such as mute of administration, the species of mammal, general health and tolerances of the mammal, weight, sex and age of the mammal, the nature and severity of the disease being treated and the like. Additionally, it is to be noted that the exact dosage of each individual compound employed in similar situations will vary. Generally, a dosage would be in the range of from about 0.1 to about 100 nanogram or more per kilogram of body weight, and usually from 1 to about 20 nanogram per kilogram of body weight.

Biological Deposit

Samples of the 454A12 hybriodoma was deposited with the In Vitro International, Inc., Ann Arbor, Mich., U.S.A., on Jun. 18, 1985, under the Accession No. IVI10075, pursuant to the provisions of the Budapest Treaty, and were transferred to the American Type Culture Collection (ATCC), 12301 Parklawn Drive, Rockville, Md. 20852 U.S.A. on Jun. 20, 1991 and assigned Accession No. HB 10804. The accession number indicated was assigned after successful viability testing, and the requisite fees were paid. The deposits were made under the provisions of the Budapest Treaty on the International Recognition of the Deposit of Microorganisms for the Purpose of Patent Procedure and the Regulations thereunder (Budapest Treaty). This assures maintenance of viable cultures for a period of thirty (30) years from the date of deposit and at least five (5) years after the most recent request for the furnishing of a sample of the deposit by the depository. The organisms will be made available by the ATCC under the terms of the Budapest Treaty, which assures permanent and unrestricted availability of the cultures to one determined by the U.S. Commissioner of Patents and Trademarks to be entitled thereto according to 35 U.S.C. §122 and the Commissioner's rules pursuant thereto (including 37 CFR §1.12).

The present invention has been described with reference to specific embodiments. However, this application is intended to cover those changes and substitutions which may be made by those skilled in the art without departing from the spirit and the scope of the appended claims.

We claim:

1. A method of treating a nonmalignant hyperproliferating ocular epithelial or endothelial cell condition comprising exposing said hyperproliferating cells to a concentration of toxin conjugate sufficient to kill the hyperproliferating cells, wherein said toxin conjugate comprises: (a) an antigen binding portion of an antibody capable of binding to a transferrin growth factor receptor without competing with binding of transferrin to the transferrin growth factor receptor; and (b) a plant toxin molecule.

2. The method of claim 1, wherein said exposure of the hyperproliferating cells to the toxin conjugate is by local administration.

3. The method of claim 2, wherein the antibody is monoclonal antibody 454A12 produced by a hybridoma on deposit with the ATCC with Accession No. HB 10804.

4. The method of claim 3, wherein the plant toxin molecule is ricin A.

5. The method of claim 4, wherein said hyperproliferative ocular epithelial or endothelial cell condition is selected from the group consisting of epithelial down growth, vitreoretinopathy, blockage of drainage passage after glaucoma surgery, cicatricial penthagoid, pterygium, and diabetic retinopathy.

6. A method of treating a patient in need of treatment of a nonmalignant hyperproliferating ocular epithelial or endothelial cell condition, the method comprising administering to said patient an amount of a toxin conjugate sufficient to kill said hyperproliferating cells, wherein said toxin conjugate comprises: (a) an antigen binding portion of an antibody capable of binding to a transferrin growth factor receptor without competing with binding of transferrin to the transferrin growth factor receptor; and (b) a plant toxin molecule.

7. The method of claim 6, wherein said toxin conjugate is administered locally to said hyperproliferative cells.

8. The method of claim 7, wherein the antibody is monoclonal antibody 454A12 produced by a hybridoma on deposit with the ATCC with Accession No. HB 10804.

9. The method of claim 8, wherein the plant toxin molecule is ricin A.

10. The method of claim 9, wherein said hyperproliferative ocular epithelial or endothelial cell condition is selected from the group consisting of epithelial down growth, vitreoretinopathy, blockage of drainage passage after glaucoma surgery, cicatricial penthagoid, pterygium, and diabetic retinopathy.

* * * * *